United States Patent
Mehta

[19]

[11] Patent Number: 6,122,599
[45] Date of Patent: Sep. 19, 2000

[54] APPARATUS AND METHOD FOR ANALYZING PARTICLES

[76] Inventor: Shailesh Mehta, 9-B Poplar, Eden Woods, Thane (W), India, 400 601

[21] Appl. No.: 09/023,207

[22] Filed: Feb. 13, 1998

[51] Int. Cl.[7] .................................................. G01N 15/02
[52] U.S. Cl. ............................................. 702/100; 702/29
[58] Field of Search ............................... 702/29, 26, 100; 324/464

[56] References Cited

U.S. PATENT DOCUMENTS

| | | | |
|---|---|---|---|
| 2,656,508 | 10/1953 | Coulter | 324/71.1 |
| 3,689,833 | 9/1972 | Hogg | 324/71 |
| 3,910,702 | 10/1975 | Corll | 356/72 |
| 3,949,197 | 4/1976 | Bader | 235/92 |
| 3,968,429 | 7/1976 | Coulter et al. | 324/71 |
| 3,979,669 | 9/1976 | Godin | 324/71 |
| 3,982,182 | 9/1976 | Hogg | 324/71 |
| 3,984,307 | 10/1976 | Kamentsky et al. | 209/74 R |
| 4,009,443 | 2/1977 | Coulter et al. | 328/111 |
| 4,019,134 | 4/1977 | Hogg | 324/71 |
| 4,078,211 | 3/1978 | Longman, Jr. | 324/71 |
| 4,081,340 | 3/1978 | Zimmermann et al. | 204/180 |
| 4,103,229 | 7/1978 | Gear | 324/71 |
| 4,161,690 | 7/1979 | Feier | 324/71 |
| 4,198,160 | 4/1980 | Kachel et al. | 356/72 |
| 4,220,916 | 9/1980 | Zimmermann et al. | 324/71 |
| 4,237,416 | 12/1980 | Zöld | 324/71 |
| 4,298,836 | 11/1981 | Groves et al. | 324/71 |
| 4,348,107 | 9/1982 | Leif | 356/72 |
| 4,368,423 | 1/1983 | Liburdy | 324/65 |
| 4,420,720 | 12/1983 | Newton et al. | 324/71.4 |
| 4,438,390 | 3/1984 | Hogg | 324/71.1 |
| 4,440,638 | 4/1984 | Judy et al. | 210/198.2 |
| 4,472,506 | 9/1984 | Liburdy | 436/63 |
| 4,484,134 | 11/1984 | Halloran | 324/71.1 |
| 4,527,114 | 7/1985 | Coulter | 324/71.1 |
| 4,535,284 | 8/1985 | Groves et al. | 324/71.1 |
| 4,596,464 | 6/1986 | Hoffman et al. | 356/336 |
| 4,791,355 | 12/1988 | Coulter et al. | 324/71.1 |
| 4,797,624 | 1/1989 | Dunstan et al. | 328/114 |
| 4,972,137 | 11/1990 | Dunstan et al. | 324/71.4 |
| 5,128,257 | 7/1992 | Baer | 435/173 |
| 5,130,639 | 7/1992 | Hachey | 324/71.4 |
| 5,137,817 | 8/1992 | Busta et al. | 435/173 |
| 5,247,461 | 9/1993 | Berg et al. | 364/555 |
| 5,376,878 | 12/1994 | Fisher | 324/71.4 |
| 5,526,808 | 6/1996 | Kaminsky | 128/632 |
| 5,532,943 | 7/1996 | Asano et al. | 364/555 |
| 5,576,617 | 11/1996 | Webb et al. | 329/71.4 |

*Primary Examiner*—Timothy P. Callahan
*Assistant Examiner*—Linh Nguyen
*Attorney, Agent, or Firm*—Chittaranjan Nirmel; Jones Jain, L.L.P.

[57] ABSTRACT

An apparatus for analyzing particles suspended in a fluid. The fluid has electrical properties different from that of the particles. The fluid and particles move from a first fluid containing portion to a second fluid containing portion through a conduit or aperture. A first pair of electrodes, each electrode of the pair being in a respective fluid containing portion. A constricted electrical path is defined between the first and second electrodes, and the path extends along the aperture. At least one other pair of electrodes is positioned in a non-encircling arrangement, and are aligned with each other and transversed to the constricted electrical path. This configuration eliminates many common errors suseptible to other devices.

33 Claims, 11 Drawing Sheets

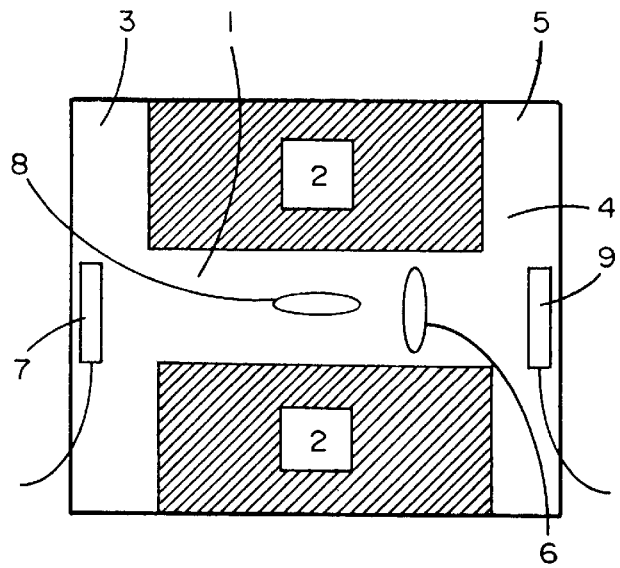
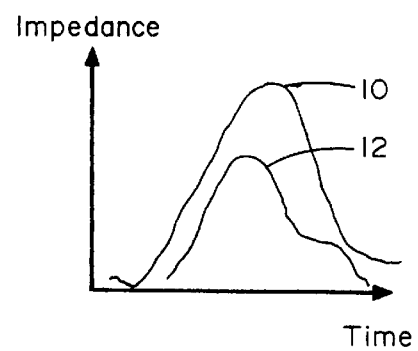
FIG. 1
PRIOR ART
FIG. 2
PRIOR ART
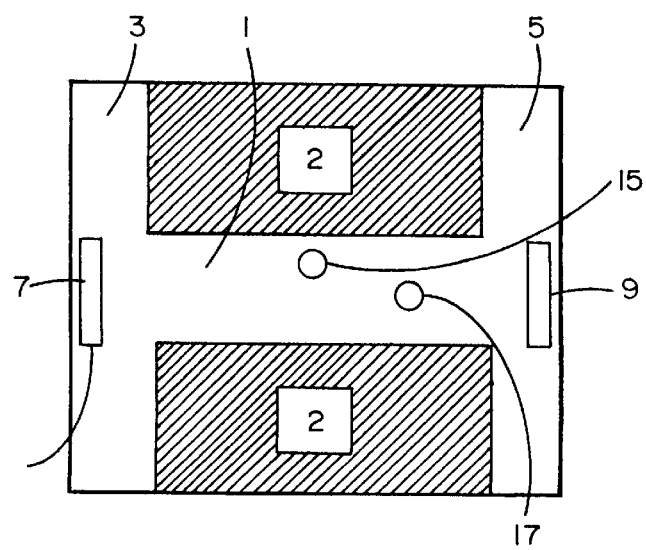
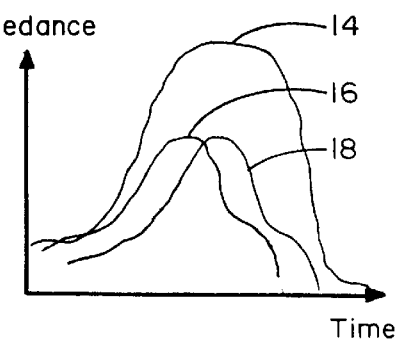
FIG. 3
PRIOR ART
FIG. 4
PRIOR ART

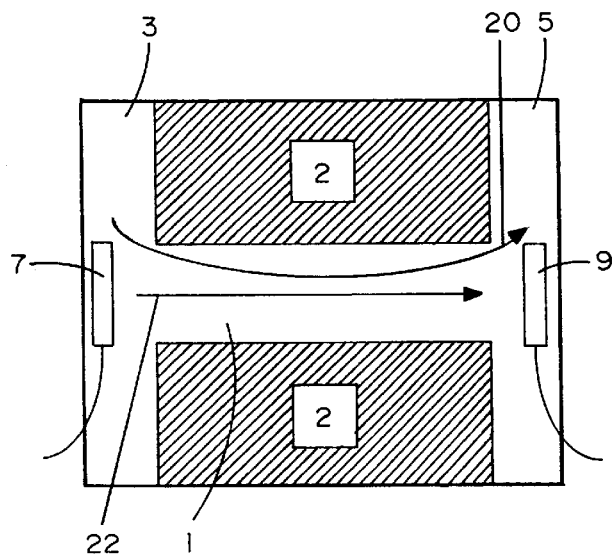
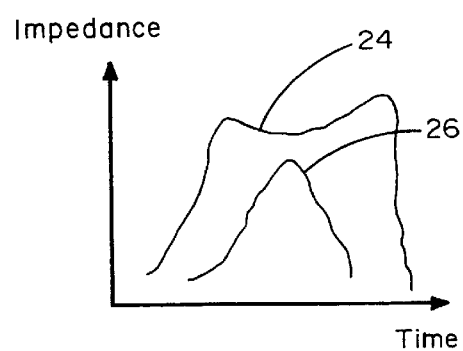
FIG. 5
PRIOR ART
FIG. 6
PRIOR ART
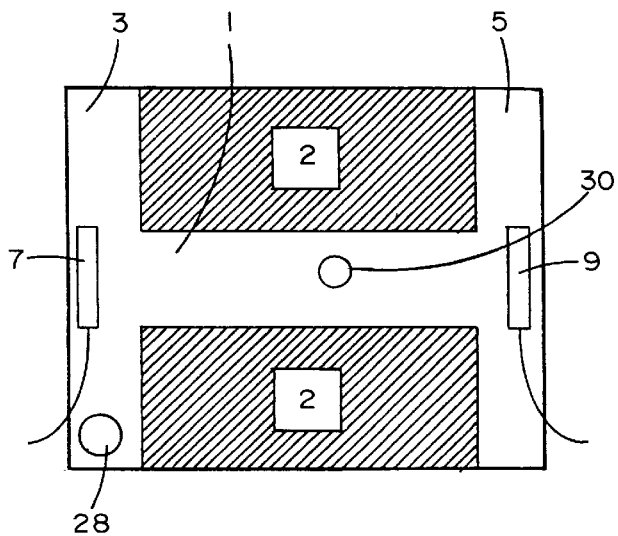
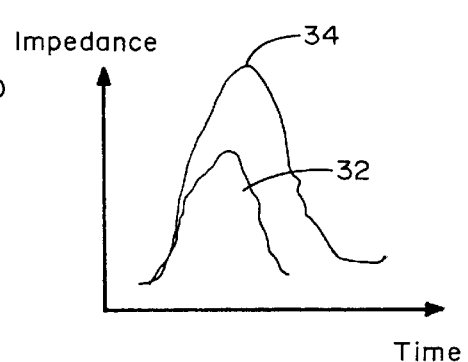
FIG. 7
PRIOR ART
FIG. 8
PRIOR ART

APPARATUS AND METHOD FOR ANALYZING PARTICLES

FIELD OF THE INVENTION

This invention relates to an apparatus and method for analyzing particles suspended in a fluid. More particularly, this invention relates to an apparatus for counting, measuring, differentiating, manipulating, and controlling the movement of particles suspended in a fluid having electrical properties different from that of the particles by determining electro-physical properties, e.g., electrical impedance, of the particles.

BACKGROUND OF THE INVENTION

U.S. Pat. No. 2,656,508 to Coulter discloses what is commonly referred to as the "aperture impedance" or the "Coulter" principle for counting and sizing particles. An exemplary arrangement utilizing this principle is shown in FIGS. 1, 3, 5, and 7. Through a small aperture 1, the fluid 4 containing the particles in dilute suspension is aspirated from one electrically insulating vessel 3 into another similar vessel 5. This aperture 1 provides the only path for fluid or electrical communication between the two vessels 3 and 5. One electrode 7 is immersed in the fluid in the first vessel 3, and a second electrode 9 is immersed in the fluid in the other vessel 5. The passage of a particle through the aperture 1 causes a brief change in electrical impedance measured between the two electrodes 7 and 9. The magnitude of the transient resistance change, called a "resistive pulse", is a measure proportional to the size of the particle. Several thousand particles may be measured in a few seconds, and the data may be sorted into classes to provide a distribution histogram showing the number of particles falling into each size range. However, this basic arrangement has suffered drawbacks, and drawbacks in accuracy can be significant. For example, measurement of particle size range is critical for the production of a wide range of products including ceramics; toners; dyes; powders; cement; sugar; pharmaceutical products and photographic materials. Variations in particle size can critically influence both the manufacturing processes and the characteristics of the final product.

There have been many attempts to address the drawbacks associated with this basic design. However, none of these attempts have been entirely successful. These drawbacks have resulted in limitations to the smallest particle that can be measured with a given aperture size, orientation errors, coincidence errors, trajectory errors, and extended sensing zone errors.

For small particles, the electrical and acoustic noise compete with the small resistive pulse signal generated by the particles resulting in low S/N ratio. Therefore, the smallest particle measurable by the aperture impedance principle is typically 2% of the aperture diameter. With very small apertures, such as a sub-micrometer aperture, the lower limit is higher than 2% because the noise floor rises substantially due to the increased resistance. The noise goes as the square root of the aperture resistance and the aperture resistance is inversely proportional to the square of the aperture cross-sectional area. Therefore, as the aperture becomes smaller, the resistance increases and so does the associated noise. Additionally, for the instruments based on this aperture impedance or electrical sensing zone method, in the measurement of small particles, thermal aperture noise continues to exceed all other noise contributions by more than an order of magnitude. Further improvements in the circuitry cannot lead to better resolution.

The prior art embodiment of FIG. 1 does not take into account the shape of the particle and this leads to an inability to obtain important information about the particles and significant particle orientation errors. The electrical response for cylindrical shaped particles measured by this aperture impedance method can be proportional to the size deduced from a calibration using spherical particles. This may be errors as high as 25%. There is a complex relationship between hydrodynamic forces, deformation of particles, aperture dimensions and pressure and therefore it is not possible to relate the characteristics of the pulse to the shape of the particle.

In an attempt to get more information on the particles, prior art designs have simultaneously passed high and low-frequency currents through the aperture. While the use of appropriate filtering techniques can permit detection of both the low frequency resistance and high frequency reactance of the particle traversing the aperture, the interference created between the two separate current sources employed to create the high frequency and the low frequency current within the aperture cannot be eliminated. Any slight change in conditions can cause either, or both of the two frequencies to become de-tuned.

Further, it is known that generally, due to the hydrodynamic focusing in most instruments, elongated particles will be aligned with their elongated axis substantially parallel to the center axis of the orifice. With two particles of equal volume, one being spherical and one being elongated, the spherical particle while passing thorough the orifice will have a greater cross section perpendicular to the current flow than the elongated particle. Hence, the spherical particle will distort the field in such a manner that it will give a greater measured size than the elongated particle, despite their equal volumes.

FIGS. 1 and 2 illustrate the error in the prior art due to the difference in orientation of the particles. Aperture 1 in the insulator 2 establishes the constricted electrical path of external electrodes. Consider a non-spherical particle 8 with its main axis along the aperture axis, and another non-spherical particle 6 with its main axis perpendicular to the aperture axis. The particle 6 with its main axis perpendicular the aperture axis would obstruct the electric field in the aperture 1 significantly more, and would result in a higher peak 10 as compared to the peak 12 of other particle 8 with its main axis along or parallel to the aperture axis. Thus, it is evident that particle size measurements for non-spherical particles can be fairly erroneous.

Another limitation with prior art devices results in certain instruments counting losses of up to 20% due to random coincidences of particles in the orifice. Simultaneous presence of more than one particle in the aperture can occur without detection. The prior art neglects the co-incident pulses most of the time or provides imprecise corrections. Statistical methods are used to compensate for neglecting these pulses. This inherently limits the accuracy of the instrument. FIGS. 3 and 4 illustrate the error in the prior art due to the co-incident presence of particles in the sensing zone. Assume that a second particle 15 enters the sensing zone before a first particle 17 has left the sensing zone. The result is that the pulse 16 due to the first particle 17 is superimposed with the pulse 18 due to the second particle 15 resulting in a much larger pulse 14.

An additional problem in the prior art is due to trajectory errors. This may arise due to non-uniform current density at different cross-sectional locations within the aperture of the instrument. Because of the non-uniform current density, the pulse height of the related shape depends on the path an individual particle takes through the aperture. The current density is significantly higher at the edges of the entrance and exit of the aperture. Also, the electrolyte stream velocity is higher in the center of the aperture than in the periphery due to boundary development. Some particles approaching the aperture obliquely travel close to the wall. These particles move slower than those that pass through the center of the aperture. The particles enter and leave the aperture boundaries through the zones of higher current density and may suffer shape distortions as a result of higher shear force near the wall resulting from the higher stream rate associated with the boundary layer. Errors may therefore result because pulse width measurements of larger particles moving in the center of the aperture might be quite similar to pulse width measurements of smaller particles moving near the aperture walls. For example, a particle traveling close to the wall of the aperture produces an 'M'-shaped pulse. The pulse-height of this particle is significantly higher in comparison to the normal pulse due to a particle traveling through the center of the aperture. The resultant size distribution of a nearly mono-sized particle population is then strongly skewed toward higher volume. A true representation of the real size of the particle thus cannot be obtained. FIGS. 5 and 6 illustrate the error in the prior art due to the difference in the trajectory of the particle passing through the sensing zone. As the field lines are concentrated near the walls, a particle following a trajectory 20 which is close to the walls, gives a pulse 24 of higher magnitude in comparison to the pulse 26 associated particle that follows a trajectory 22 close to the axis of the aperture 1.

Besides the limitation on the smallest particle that can be measured with a given aperture, and the other drawbacks described above, the dynamic range of measurement is also limited. When a particle-free electrolyte passes through the aperture, the noise generated is mainly due to the electrical noise of the amplifier system. However, the noise increases greatly when a suspension of particles passes through the aperture. The absolute value of the noise increases with the increase in the size of particles. This happens partly because the particles moving just outside the aperture alter the conductivity gradient in the aperture. If the magnitude of this disturbance is greater than the signal due to the small particles, the measurement of small particles becomes impractical. Thus, the measurable range of sizes is limited, and it becomes difficult to distinguish between large and small particles in the same suspension.

Another limitation related to this phenomenon is an extended sensing zone error that occurs due to particles moving just outside the aperture. These external particles alter the conductivity gradient in the aperture. FIGS. 7 and 8 illustrate the error in the prior art due to the disturbance of extended sensing zone by particles outside the aperture. A large particle 28 located just outside the aperture 1 can significantly alter the signal on the electrodes 7 and 9, even before it enters the aperture 1. The peak 34 produced by this particle overshadows the peak 32 of a smaller particle 30 within the aperture 1 itself. Measurement of small particles in the presence of such interfering larger particles is thus impractical, when the magnitude of the disturbance is greater than the signal associated with the small particle. Thus, the range of overall sizes that can be measured becomes limited, and the ability to distinguish between large and small particles in the same suspension is hampered.

Disturbances depend upon the turbulence of the liquid at the boundary and the fringe effects of the electrical measuring fields. One phenomenon which should be mentioned as especially disturbing is that turbulence exists in the container which is located at the outlet of the channel in the through-flow direction. This turbulence recycles particles which have already been measured back into the region of the measuring field. Particles which have been recirculated in this manner re-trigger a change in the measured potential difference, thus falsifying the measurement result. It has already been proposed to provide a spatial limiting of the suspension in the channel. However, the equipment suitable for exploiting this technique is extremely complicated and correspondingly expensive. U.S. Pat. No. 4,161,690 addresses the recirculation problem by triggering sampling via the Coulter electrodes when the particle's passage through the middle of the channel is detected by a center electrode.

Thus, there is a requirement for an apparatus which can measure particle size and other properties more accurately than existing apparatus. If the particle measurements can be done more accurately and speedily the process for separation of different particles also improves. Counting, measuring, differentiating, separating and controlling the movement of particles is very critical in numerous industries like ceramics, cosmetics, explosives, powdered fuel, metal powder, abrasive, minerals, pharmaceutical, pigments, fillers, bio-technology and the like. Various parameters like volume, shape, rigidity, resistance and reactance have become extremely important in characterizing the properties of the particles and the fluid carrying the particles.

SUMMARY OF THE INVENTION

This invention relates to an apparatus and a method to measure accurately and at a faster rate, the size and number of particles suspended in a fluid using the aperture impedance principle.

It is a further objective of the invention to improve the dynamic range of measurement, to characterize particles at multiple frequencies, to obtain information on shape of particles, and to measure more accurately the velocities of particles flowing through an aperture.

It is a further objective of the invention to improve the signal-to-noise ratio by using signal correlation techniques and providing on-chip signal analysis circuitry.

It is a further objective of the invention to do impedance computer tomography on individual particles, to make impedance measurements at multiple frequencies, and to get detailed information on the shape and internal structure of the particles.

It is a further objective of the invention to control the movement and orientation of particles when present in an aperture in the transducer and to measure the velocity of the particle in the transducer more accurately.

A further objective of the invention is to physically separate different types of particles.

Its a further objective of the invention to cause the breakdown of the cell membrane of the cell passing through the transducer in a controlled way.

In accordance with another aspect of the invention, the transducer is used in conjunction with a particle separator which ejects the fluid carrying the particle in the form of small charged droplets, which can be separated by controlling the electric field along the path of the droplet.

Further objects will become evident from the detailed description of the invention.

BRIEF DESCRIPTION OF THE DRAWINGS

The invention can be better understood in the light of various features and aspects described in the illustrations wherein:

FIG. 1 illustrates the error in the prior art due to the difference in orientation of the particles;

FIG. 2 as a graphical illustration of the errors occurring from FIG. 1;

FIG. 3 illustrates the error in the prior art due to the co-incident presence of particles in the sensing zone;

FIG. 4 as a graphical illustration of the errors occurring from FIG. 3;

FIG. 5 illustrates the error in the prior art due to the difference in the trajectory of the particle passing through the sensing zone;

FIG. 6 as a graphical illustration of the errors occurring from FIG. 5;

FIG. 7 illustrates the error in the prior art due to the extended sensing zone being disturbed by particles outside the aperture;

FIG. 8 as a graphical illustration of the errors occurring from FIG. 7;

DETAILED DESCRIPTION OF THE INVENTION

Unless defined otherwise, all scientific or technical terms or phrases used herein have the same meaning as commonly understood by one of ordinary skill in the art to which this invention belongs. Unless specifically mentioned otherwise, the methods and materials used or contemplated herein are those that are well known and ordinarily practiced in the art. Additionally, the following terms are defined:

The term "substrate" used herein means an insulating or semiconducting material.

When an electrode is used for introducing or injecting the signal into the constricted electrical path, it is an active functional as electrode. When an electrode is used for measuring the change in signal, it is referred to as passive electrode. An electrode can be in both active and passive modes simultaneously.

The term "constricted electrical path" used herein means a volume between a pair of active electrodes in which a substantial current is established between related the electrodes, the related electric field being substantially restricted to the constricted electrical path.

An "encircling" arrangement is a physical relationship between two elements, e.g., electrodes, where one element entirely or substantially entirely extends around and encircles the other element. A "non-encircling" arrangement is any physical relationship between two elements other than an encircling arrangement.

The term "substantially unobstructed" with respect to the flow of fluid through an aperture, channel, or other fluid conduit, means that the fluid is free to travel through the channel without contacting any element spaced inward and spaced from the side wall or walls of the aperture, channel, or other fluid conduit.

One of the basic requirements of the invention is that there must be a difference between the electrical conductivity of the particle and the fluid in which it is suspended. Conductivity difference between the fluid and the particles can be changed by using any well-known method. For example, this can be done simply by adding an electrolyte to the fluid to increase its conductivity or by diluting the fluid with other non-conducting fluids such as distilled water to decrease its conductivity. The suspension is preferably diluted to a point where the particles suspended in the fluid medium are relatively scattered. This ensures that during particle measurement there will be a reduced possibility of two particles being present in the sensing zone simultaneously.

Figure 10:
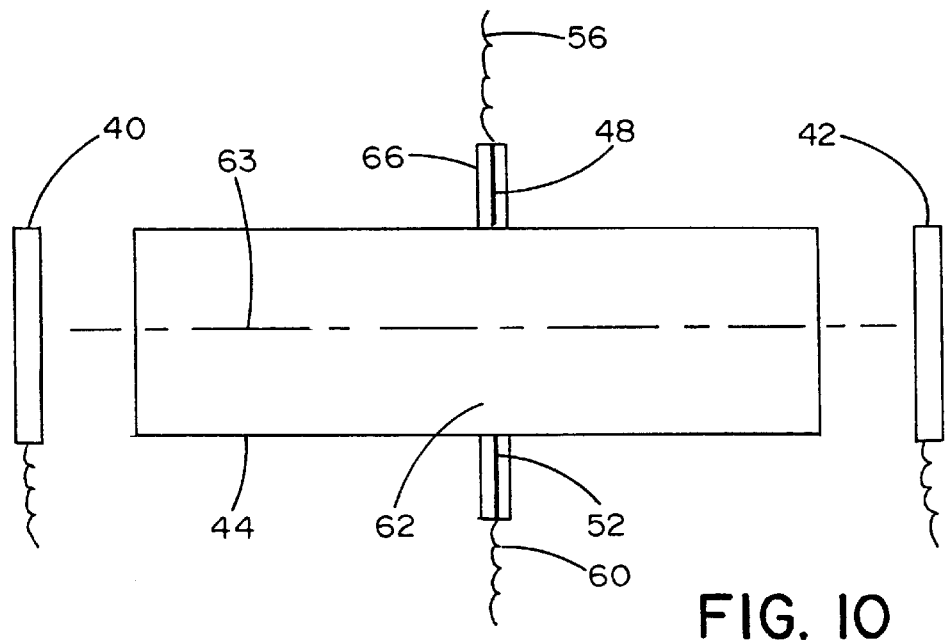
FIG. 10 is a cross sectional view of the transducer taken through line 10—10 of FIG. 9 illustrating a possible position of planar electrodes on the aperture.
Figure 9:
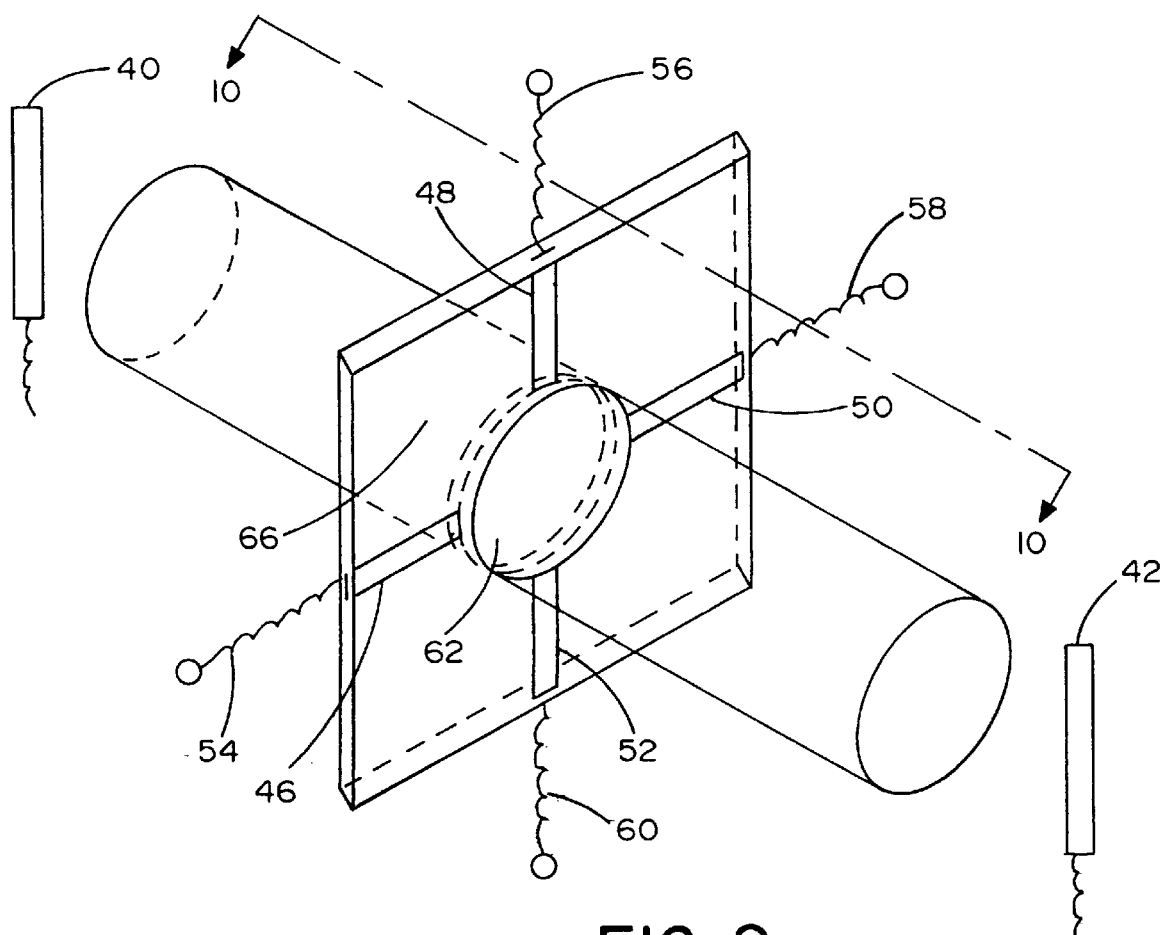
FIG. 9 is a perspective view of the transducer with a set of planar electrode array.
Figure 11:
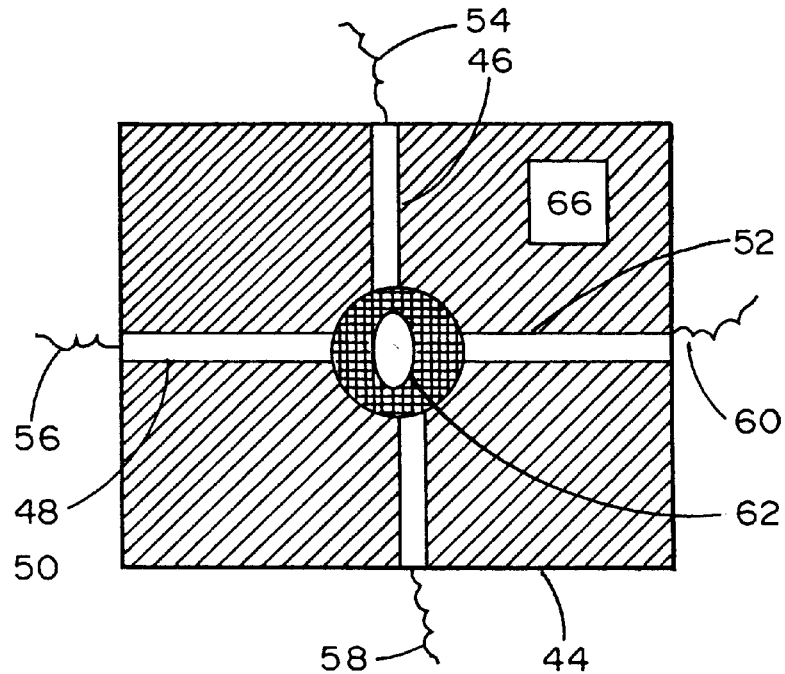
FIG. 11 is cross sectional views of FIG. 9 taken in a direction transverse from FIG. 10.

FIGS. 9–11 are schematic views of the transducer illustrating the position of the planar electrodes in relation to the external electrodes. FIG. 9 is a perspective view of the transducer with a set of planar electrode array. FIGS. 10 and 11 are sectional views of the transducer illustrating a possible position of planar electrodes on the aperture. Transducer 44 is sealingly provided between two insulating containers, vessels, or other fluid holding elements, not shown, that contain external electrodes 40 and 42 respectively. The only path for the passage of current from external electrode 40 in one container to the external electrode 42 in other container, is through the conduit or aperture 62 in the transducer 44. The only path for the passage of the fluid sample from one container to another is through the aperture. This establishes a constricted electrical path of external electrodes within the aperture and along its longitudinal axis. The hole or aperture in the transducer may be cylindrical or of any other suitable shape. A cylindrical hole helps in maintaining a uniform flow through the transducer and establishes an axially symmetrical field for external electrodes. A cylindrical hole can be easily made by ultrasonic drilling, laser drilling, etched particle track process, standard techniques of micro-electronics like wet or dry plasma etching, electron beam milling and the like. The aperture is shown much larger in comparison to the external electrodes to illustrate the details of the design.

In addition to the external electrodes 40, 42, planar electrodes 46, 48, 50, 52 are placed on or immediately adjacent to the internal wall, e.g., the circumference, of the aperture 62. Planar electrodes are coupled to signal generating circuitry 51 and signal analysis circuitry 53 through connections 54, 56, 58, 60. A constricted electrical path is established by coupling the output of the signal generating circuitry 51 to any pair of active electrodes. The passage of a particle through the constricted electrical path causes a measurable change in current or voltage at passive electrodes. The passive electrodes are coupled to signal analysis circuitry 53. Any of the planar or external electrodes can be used as active or passive electrodes, and as described below, the electrodes can be switched between operation as an active electrode and a passive electrode. The change in signal may also be measured at the active electrode itself, which may be advantageous in certain applications.

Only the tip of the electrode facing the hole is exposed to the fluid. The area of conducting material that is exposed to the fluid in the aperture is preferably between from 1 micron square to a few hundred micron squares. If the suspending fluid is an electrolyte, reducing the area of electrode that is exposed to the fluid results in a rising value of the electrode-electrolyte impedance at the electrode-fluid interface. Electrode-electrolyte impedance is inversely proportional to the area. There are numerous techniques known in the art for increasing the effective area of the metals such as coating with platinum black.

To distinguish a signal from the noise of the passive electrode, a significant current should be flowing through the electrodes. Precautions should be taken to avoid polarization of this small electrode. The effects of polarization can be reduced by using a high frequency AC voltage rather than DC voltage, or by creating the constricted electrical path for a shorter duration. Any variations in the electrode area can be compensated for by suitably adjusting the gain associated with that electrode.

When planar electrodes 46, 48, 50, 52 are used in the active mode, they establish another constricted electrical path. If the active pair is located opposite from each other, they establish a constricted electrical path transverse and substantially perpendicular to the longitudinal axis of the aperture. In many applications it is advantageous to use a floating signal source to minimize the interference between multiple constricted electrical paths. Two or more planar electrodes 46, 48, 50, and 52 may be used for establishing the constricted electrical path and this is subsequently referred to as a constricted electrical path of planar electrodes. The constricted electrical path can also be made using a combination of planar and external electrodes or a combination of planar electrodes in different planes. The constricted electrical path of planar electrodes and constricted electrical path of external electrodes can be established simultaneously or independently of each other.

The constricted electrical path is generated by feeding current (or applying a voltage) through active electrodes and then measuring the resulting variation in voltage (or current) as particles pass through the constricted electrical path. The simple occurrence of a pulse caused by particles entering and subsequently leaving the constricted electrical path allows the number of particles to be counted. The size of the particle may be derived from the magnitude of the pulse. The aperture size is normally chosen such that the majority of particles preferably lie within 2% to 60% of the aperture diameter.

When a particle enters the constricted electrical path, the resistance between the measuring electrodes rises if the resistivity of the particle is more than that of the fluid in which it is suspended, which is preferable. Thus, whenever a particle is present in the constricted electrical path 64, it modifies the electric field and this change may be measured at passive electrodes located in the constricted electrical path or by measuring the voltages the electrodes generating the constricted electrical path. The passive electrodes 48, 52, not used for creating the constricted electrical path, are said to be in a passive mode. Both external and planar electrodes may be used for measuring the change in the electric field within the aperture due to the passage of the particle. In one embodiment, the planar electrodes on one plane are used in passive mode and measure the signal due to the passage of a particle through the constricted electrical path established by external electrodes or the constricted electrical path of another pair of planar electrodes.

All of the planar electrodes may also be used as the passive electrodes. In such an arrangement, whenever a particle passes through the constricted electrical path along the length of the aperture, it alters the impedance between the external electrodes. This results in a measurable change in current/voltage on the external electrodes 40, 42. The passage of the particle also results in a measurable change in signal at the planar electrodes within the aperture. The aspirated particle generates a pulse, detected as a change in the current or voltage at the external or planar electrodes, as they traverse the aperture. The signal at the planar electrodes in conjunction with the signal at the external electrodes is analyzed to get detailed information on the particles. Optionally, planar electrodes 46, 48, 50, 52 may be sandwiched between two insulating or semi-conducting substrates having a through aperture 62 and around the circumference of the aperture 62.

The fluid sample of known dilution is placed in an apparatus suitable for carrying out the necessary measurements as is well known in the prior art. The fluid can be made to move through the aperture using a piston arrangement, under a positive or negative pressure head, using a mercury column or by using a bellows arrangement. For hydro-dynamically focussing the particles, any suitable mechanism well known in the prior art can be employed. An agitator may be employed to render the suspension as homogeneous as possible during the time the measurements are taken. In one embodiment, the transducer is placed in a pipe such that some part of the fluid carrying the particles pass through the aperture of the transducer. This embodiment can be used in inaccessible places such as within pipes and process containers to monitor samples on-line and remotely. In another embodiment, the transducer is sealingly placed between two containers, in such a way that the fluid carrying the particles passes through the aperture of the transducer.

Figure 14:
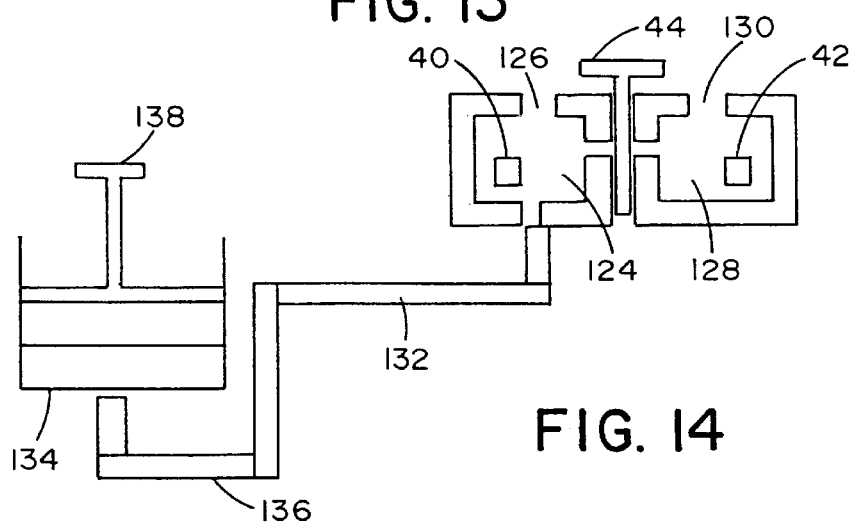
FIG. 14 shows an alternative embodiment to FIG. 13.

For certain applications it might be essential to have a constant flow. FIG. 14 illustrates an embodiment providing such a capability. According to this embodiment, the liquid is made to flow under a negative pressure head. A container 124 is connected to a mercury reservoir 134 placed at a level lower than the container through a connecting tube 136 that has a horizontal section 132 near the container end. By applying pressure on the plunger 138 of the mercury reservoir, mercury can be made to rise in the connecting tube 136 and almost reach the end of the horizontal tube. Electrolyte is placed in the container 124 through an opening 126 and then sealed. Precautions are taken to ensure that there are no air bubbles. A sample to be measured is placed in container 128 through the opening 130. The pressure on plunger 138 is released. As a result the mercury starts flowing back into the container thereby creating a negative pressure at the aperture and the particles to be measured flow through the aperture. By using electrical contacts or optical detectors, the exact amount of sample flow can be determined. The advantage of having a horizontal section 132 and a large diameter reservoir is that the pressure drop across the aperture during the measurement process remains almost during the test constant.

Figure 13:
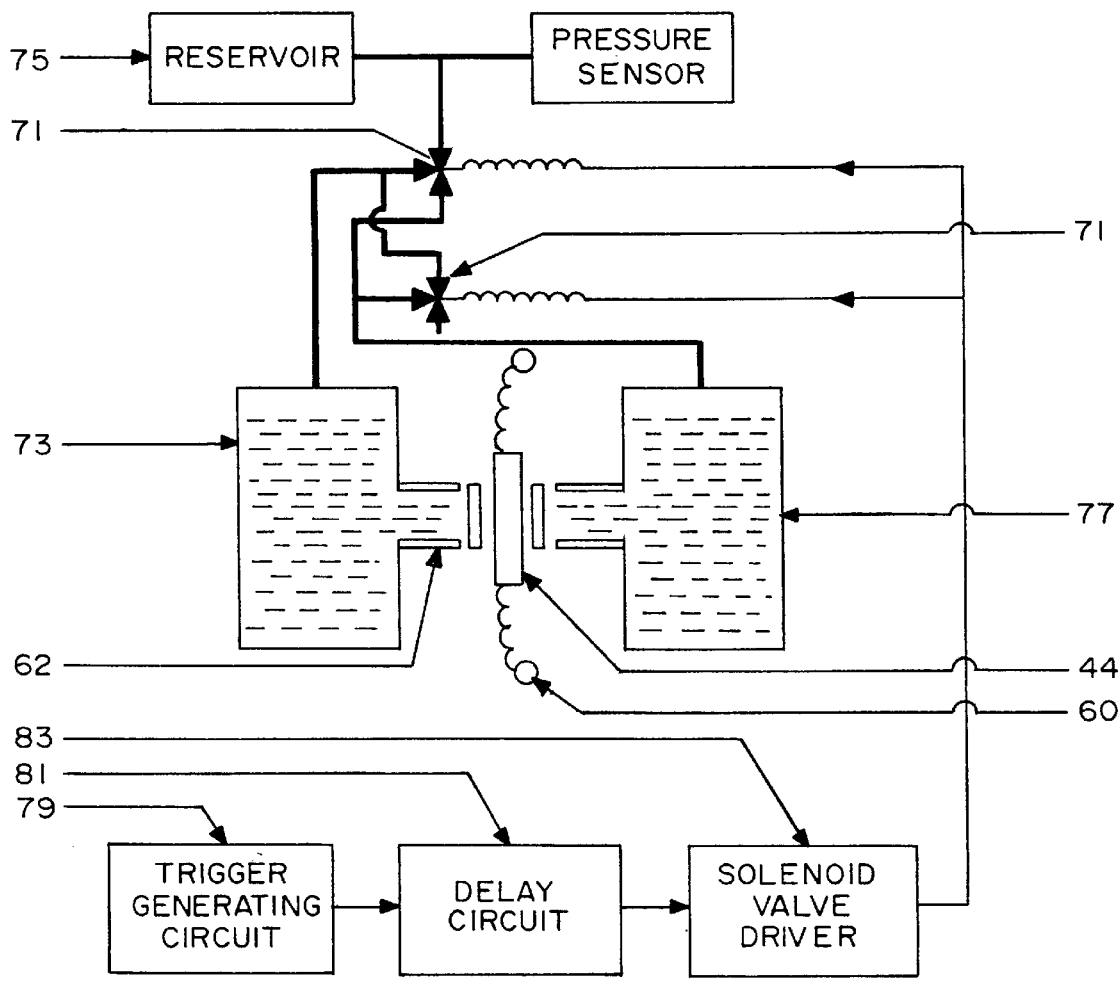
FIG. 13 schematically shows an embodiment of the invention including the containers and a mechanism for establishing the flow through the aperture.

FIG. 13 shows another embodiment the pressure differential across the transducer 44 is established by connecting the two containers 73, 77 to gas reservoirs carrying gas at different pressures. The pressure differential across the transducer 44 can be controlled in a desired way by connecting the containers to the gas reservoir through an electrically controlled pressure valve. Electrically controlled pressure valves 71 can be miniature solenoid three-way valves, wherein one end is connected to the container 73, 77, another end is connected to gas reservoir 75, and the third end is connected to the atmospheric pressure. To change the mode of the valve 71, a trigger signal is needed to energize the solenoid valve. The trigger signal is provided by the trigger generating circuitry 79 which preferably forms part of the signal generating circuitry 51 and/or the signal analysis circuitry 53. This change may occur through a delay circuit 81 and causes a solenoid valve drive 83 to change the mode of the valve. The change in the mode of the valve results in reversal of the pressure at short intervals. This can be used for studying single particle dynamics by making the particle move in and out of the aperture. This mechanism can also be used for causing selective movement of the particles from one container to the another.

The pressure differential across the transducer can be reduced to decrease the speed of the particle. By making the pressure differential negligible, the particle can be confined to the constricted electrical path, thus enabling detailed measurement on the particle. Confining the particle in the constricted electrical path could be very useful in case of impedance computer tomography measurements.

The particles can also be moved using other mechanisms like an influence of an electric field. The particles might be propelled through the apertures by electrophoretic or electro-osmotic potentials instead, or along with, the transmembrane pressure difference. Electrophoretic mobility of charged particles can be used for selective movement of particles. The additional information gained in this manner, when combined with the size measurement, would be of value in the study of colloids particularly related with zeta potential.

There are several possible methods to manufacture the transducer. In one method of manufacture, holes may drilled through gold foil tracks on an epoxy resin sandwiched between two thin sheets of glass, using a small, e.g., 350 micron, drill. However, such techniques may not be feasible to produce smaller apertures. One method to form membranes having suitably sized apertures is to prepare planar electrodes 46, 48, 50, 52 and connecting wires 54, 56, 58, 60 on the surface of a thin glass sheet. This can be done by using electron beam lithography. A coating of an etchable polymer like polyamide is laid over the thin glass sheet. Through the etchable polymer, the first portion of the pores is made, again preferably by electron beam lithography, and finally to etch connecting channels through the glass sheet to form the second portion. Substrate material could be any advanced ceramic material like high quality alumina, silicon, quartz, sapphire, glass, or kapton. However, other substrate material may also be suitable provided that it has adequate insulation properties, mechanical strength, flatness, suitability for certain manufacturing processes, and ion penetration characteristics. Using standard techniques like sputtering and vapor deposition a thin layer of metal can be fabricated. To increase the thickness of the metal deposition standard processes like electroplating can be used. A suitable electrode pattern can be created using standard lithography. However, it is recognized that other processes may be used such that they provide the proper shape and size tolerances. Preferred electrode materials include chromegold, nickel, titanium, and platinum.

Hole drilling can be done using techniques like laser or ultrasonic drilling, dry or wet etching, ion-beam milling or a combination thereof. In a preferred embodiment, the device may be produced by a combination of photo or electron-beam lithography and ion-beam machining. Other processes may also be suitable provided that they result in the desired smoothness, taper or lack of taper, and physical tolerances. This is done on any substrate suitable for the manufacture of semiconductor devices, for example silicon. This is followed by deposition of an inert insulating layer of a suitable substance, for example silicon dioxide. In this case the conductive output leads and electrodes can be made by techniques similar to those used in the manufacture of integrated circuits. An advantage of this method of production is that active semiconductor circuitry such as amplifiers and logic gates may be placed directly on the device to perform some pre-processing of the signal.

Figure 15:
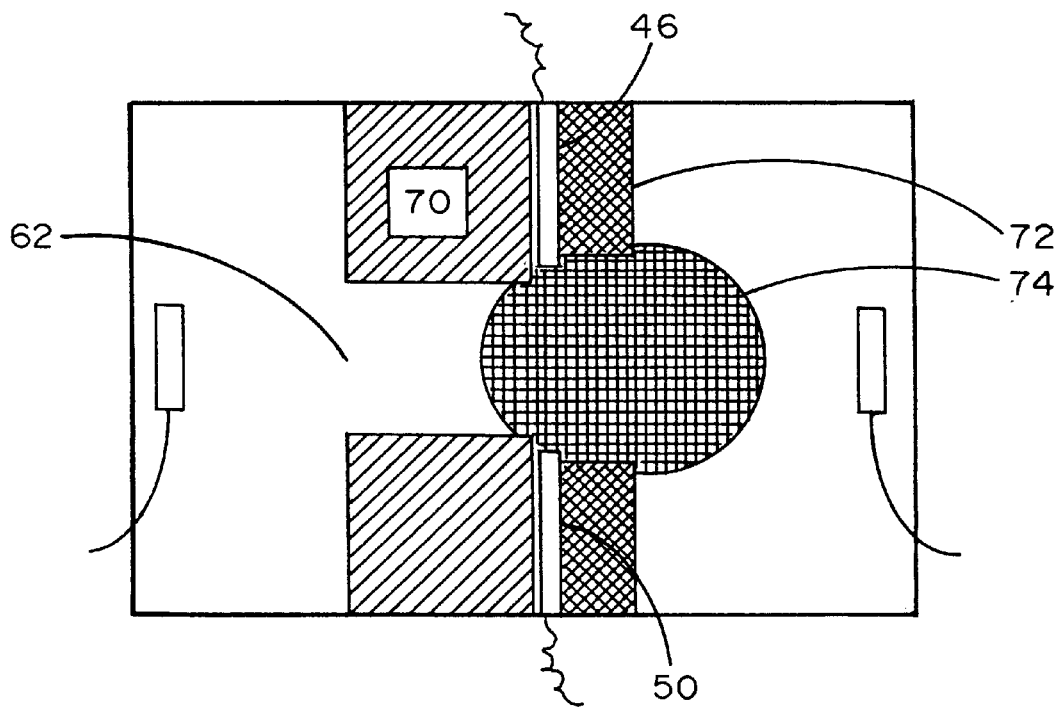
FIG. 15 is a sectional view of an alternative embodiment of the transducer with one side of the planar electrode being covered by an insulator coating.

FIG. 15 is a sectional view of an alternative transducer embodiment with one side of the planar electrode being covered by an insulator coating. In this embodiment a set of planar electrodes 46, 50 are fabricated on a substrate 70 at the end of the aperture 62 and then given an insulator coating 72. This is advantageous as it facilitates fabrication because the planar electrodes can be made using any standard technique of lithography. The insulator can be patterned using lithography techniques by exposing from either side of the aperture or by simply spin coating or can be applied using a brush. Insulator coating 72 need not cover the electrode all the way up to the aperture. The sensing zone 74 might spread outside the aperture and may be asymmetrical and non-uniform, however, this is acceptable for certain applications. For example, in case of counting particles, this does not introduce any significant errors. Preferred insulating materials include oxides, nitrides, epoxy, polyamide, and glass, and suitable application techniques, e.g., dipping, painting spraying, and electrobonding, depend upon the material chosen.

Figure 12:
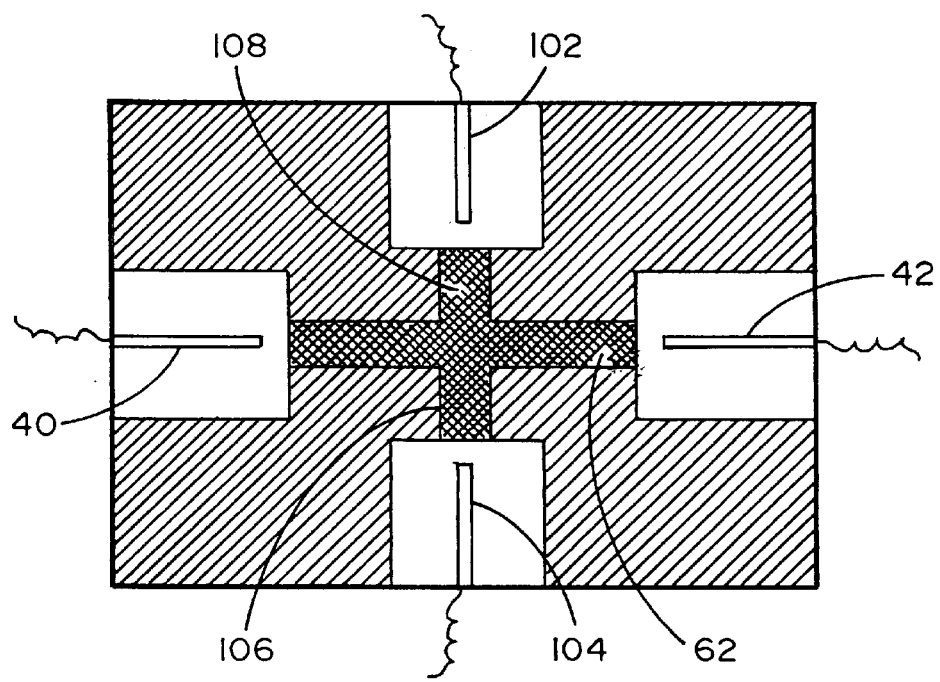
FIG. 12 is a sectional view of an alternative embodiment of the transducer where planar electrodes are formed by apertures along the plane perpendicular to the longitudinal axis of the aperture, with each supplemental aperture planar an electrode similar to the external electrode.

FIG. 12 is a sectional view of an alternative embodiment of the transducer where planar electrodes are formed by supplemental apertures 106, 108 along the plane perpendicular to the axis of the main aperture 62, and each having an electrode 102, 104 similar to external electrode. These apertures function similar to the planar metallic electrodes described earlier that were located on or immediately adjacent the aperture wall. The obvious advantage of this type of electrode is that it avoids the problems of polarization of electrodes, where the quantity and the time duration of the application of current through an electrode can damage the electrode. The diameter of these planar apertures is preferably smaller than the diameter of the main aperture. These aperture type planar electrodes 102, 104 can be made using any combination of the techniques mentioned earlier.

Signal generating circuitry 51 takes inputs from various systems to establish the constricted electrical path that is most applicable for the particular application. Signal generating circuitry 51 comprises multi-frequency current sources, multi-frequency voltage sources and a system for feeding the signal to active electrodes in various combinations comprising multiplexers, demultiplexers, amplifiers, digital-to-analog converters. Circuitry for measuring the change in voltage across or current through passive electrodes includes high pass filters, low-pass filters, demultiplexers, amplifiers, sample and hold, peak detectors, comparators, monostable multivibrators, lock-in-amplifiers, trans-conductance amplifiers, isolation amplifiers, opto-couplers, analog-to-digital converters, frequency modulators and amplitude modulators.

The high-pass filter eliminates the impact of random changes in the voltage at the electrode-electrolyte interface that normally changes very slowly. The random drift in the electrode-electrolyte impedance arises due to the complex processes occurring at the electrode-electrolyte interface and the change in the composition of the electrolyte itself as the electrolyte moves over the electrode.

In general, measurements of impedance are performed by connecting low impedance electrodes to a conductive region and driving a current between them. The resulting voltage is measured with a suitable voltmeter. To eliminate the error due to the measurements, it is usual to employ a second receiving pair of electrodes to measure the voltage. Provided that the input impedance of the voltmeter is much higher than the electrode impedance, the voltage measured per unit current through the driving electrodes is little affected by any of the four electrode impedances or fluctuations thereof. Inter-electrode capacitance and leakage capacitance that determine the noise levels and the frequency response of the transducer can be easily estimated by known methods. The ratio of the width of the pulse to the peak height of the pulse is a good measure of the gross shape of the cell. The integrated area under the pulse is a good measure of cell volume and is relatively independent of the cell shape.

Circuitry for analyzing the change in the electrical characteristics of the particles may include systems for counting, measuring, differentiating, separating, controlling, impedance computer tomography, signal-correlation, coincidence error, off-axis particles, velocity measurement, controlling pressure, and electric and magnetic fields within the transducer. A system basically comprises of an algorithm implemented through known hardware and/or software. The various systems take inputs from each other depending on the particular application. The exact nature of combining these systems depends on the particles to be distinguished, the nature of the fluid, and the size of constricted electrical path. Signal generating circuitry 51 also takes inputs from various systems to establish the constricted electrical path that is most applicable for the particular invention.

Figure 18:
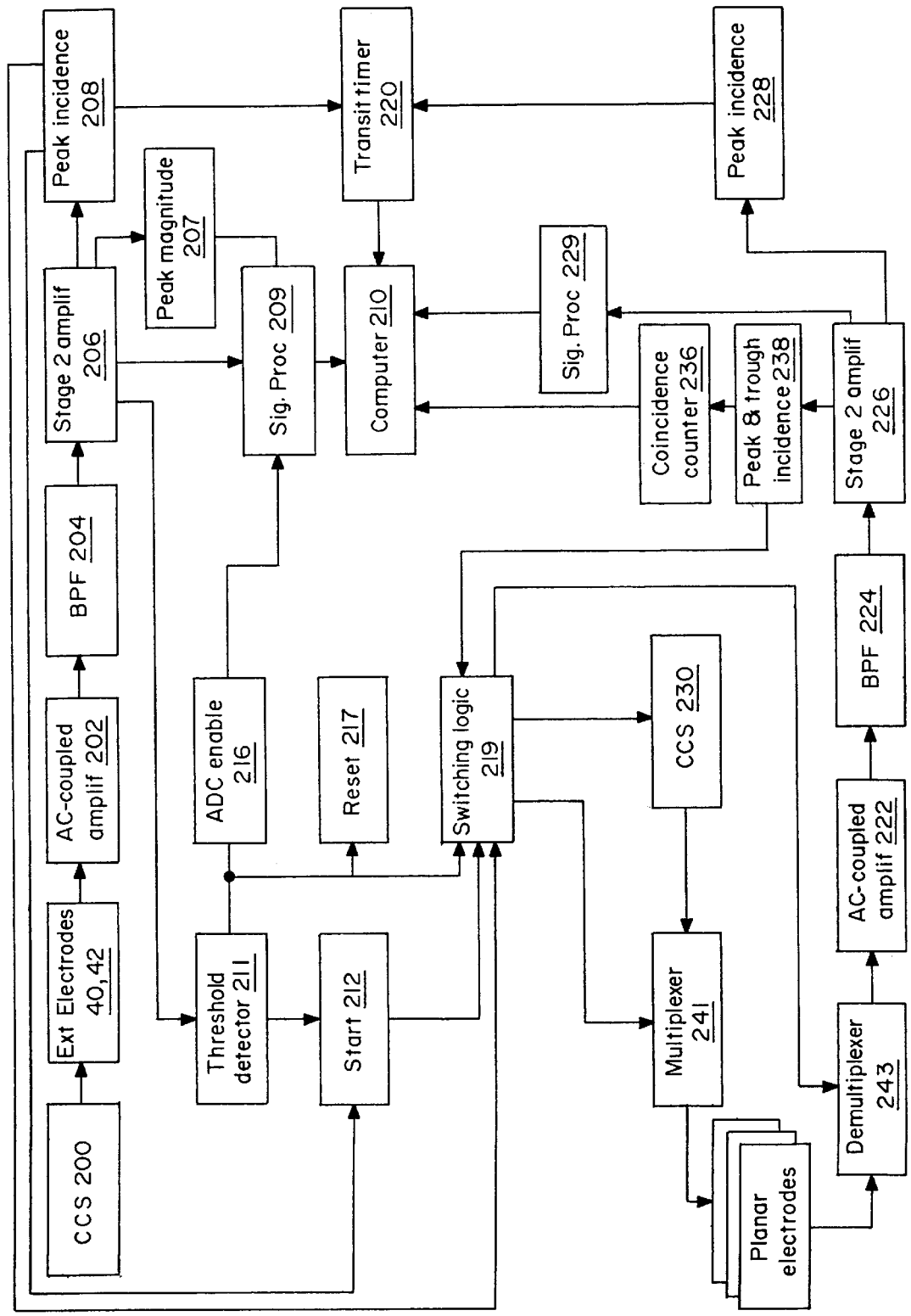
FIG. 18 is a block diagram of signal processing and control circuitry for various embodiments of the invention.

Referring to FIG. 18, an arrangement for implementing the functionality described above includes a constant current source 200 that generates a current between the external electrodes 40, 42. An amplifier 202 is AC-coupled to the external electrodes. The output of amplifier 202 is applied to a bandpass filter 204 to select a range of frequencies of the pulse generated by the particle. The bandpass filter 204 output is further amplified by a second stage amplifier 206 whose output is applied to a peak incidence detector that indicates the time of a peak (generates a pulse when a local peak is reached). The second stage amplifier output is also applied to a peak magnitude detector 207 which latches the input at the highest level detected since it was last reset. The second state amplifier output is also applied to a signal processing circuit 209 that performs various processing steps optionally including differentiation, integration, rising edge detection, trailing edge detection, Fourier transform, etc for purposes of data analysis. These data may also be digitized for application to the computer 210. The results of this signal conditioning done by signal processing block 209 are applied to a computer 210. The second state amplifier output is also applied to a threshold detector 211 that generates a square pulse whose temporal width coincides with the time the particle-generated pulse is above some predetermined level. Physically, the threshold detector remains at a high level while the particle is within the aperture. The output of peak incidence detector 208 is applied to a transit timer 220 that outputs the total time elapsed following the peak incident. The output of threshold detector 211 is applied to an ADC enable circuit 216 that indicates to signal processing circuit 209 that the trailing edge of a pulse has been detected and that it is time to sample the peak magnitude latched in peak magnitude detector 207. The output of threshold detector 211 is also applied to a reset circuit 217 that is coupled (no connections) to a number of different components to prepare them for measuring the next particle, for example, the peak magnitude detector 207. The output of threshold detector 211 is applied to a toggle circuit 218 whose output is applied to a switching logic circuit 219. Threshold detector 211 applies its output also to a start circuit 212. Start circuit 212 receives the signal from peak incidence detector 208 as well. The start circuit has a timer and a logical element that generates a pulse, responsive to the leading pulse edge, the trailing pulse edge, or some time interval following either. This pulse output by start circuit 212 is applied to switching logic 219 to initiate the application of current to the planar electrodes via a constant current source 230, however, further logic in switching logic circuit 219 is applied before the final command signal to initiate the current application, through multiplexer 241, to the planar electrodes.

Multiplexer 241 applies a voltage or current to the various planar electrodes. Multiplexer 241 receives control signals from switching logic circuit 219 to perform the following operations:

Selected combinations of planar electrodes are reverse polarized, changed from a source to a sink (both active) or changed to a passive state.

The constant current source is switched from a surrogate load (not shown, but internal to constant current circuit 230) chosen to mimic the load presented by the constricted electrical path generated by the selected active planar electrodes.

Switching logic circuit 219 is further configured, through control of a demultiplexer 243, to select combinations of planar electrodes and couple these through demultiplexer 243 for signal analysis. These can be active or passive planar electrodes.

As discussed elsewhere in this specification, depending on the embodiment of the invention, there are a number of different combinations of electrodes that can be selected for purposes of generating a constricted electrical path between them and/or for measuring a signal from them. For example, consider an embodiment with four planar electrodes such as shown in FIG. 9, with the modification that there are multiple sets of longitudinally displaced planar electrodes. Switching logic circuit 219 may command multiplexer 241 and CCS 230 to connect the planar electrodes to indicate the time of passage from the entrance region (indicated by peak incidence output by peak incidence detector 208) to the proximity of the planar electrodes. These planar electrodes may also indicate which quadrant (or in other embodiments employing more electrodes, which circumferential sector).

The duration between these two events indicates the particles average speed. Using a set of known possible trajectories the particle may follow (which can be calculated using viscous flow models or determined experimentally using laser Doppler velocimetry), the particle's radial position can be determined. (Recall that particles following a trajectory close to the wall move more slowly than ones closer to the center.) Using this data, switching logic circuit 219 may control a further array of planar electrodes downstream of the first set of planar electrodes used to sense proximity, by selecting the pair of downstream planar electrodes that would produce the highest possible current density in the immediate vicinity of the particle based on the determined radial position and the sector or quadrant the particle was determined to be in. This will create a localized constricted electrical path in the immediate proximity of the particle, which, by virtue of the fact that the particle is large relative to the size of the local restricted electrical path, will allow higher resolution. Thus a large aperture can be used to measure particles substantially smaller than it with good resolution. Other control variations are possible using the switching logic control to selected active and passive electrodes.

Signals from the planar electrodes are applied to an first amplifier 222 that is AC coupled to the planar electrodes. The amplified output of amplifier 222 is bandpass filtered by a bandpass filter 224 and applied to a second stage amplifier 226. The output of the second stage amplifier 226 is applied to a peak incidence detector 228 which outputs to transit-time timer 220. The output of the second stage amplifier 226 is also applied to a peak incidence and trough detector that detects peaks and troughs and applies a result to a coincidence counter 236. Coincidence counter 236 cumulates the number of peaks and applies this data to the computer 210. The output of second stage amplifier 226 is also applied to a signal processing circuit 229 which performs functions like those performed by signal processing circuit 209.

Note that the embodiment of FIG. 18 is an example only of how signal processing and control could be performed using discrete components. Alternatively, the pulses could be digitized and all the control and reduction steps discussed above and in other places in the specification performed through a control/data reduction program. Constant current value is adjusted in such a way that the voltage on the external electrode is typically between 0.1 to 20 Volts. The change in voltage could typically be of the order of 0.1%. Of-course the change in voltage is proportionate to cube of the radius of the particle. If the largest particle to be measured in 40 times larger than the smallest particle, the ratio of the largest peak to the smallest peak would be 64000:1. Logarithmic amplifiers or dynamic selection of amplifiers gains, can be used for coping with such a high dynamic range.

Subsequently all the data is compiled and subjected to statistical analysis and techniques like curve fitting and cluster analysis. A signal from the second stage of amplification or directly after the input stage of amplification goes to the threshold detector. A threshold detector effectively gives a pulse for the time duration for which the particle is in the constricted electrical path of the external electrode. The threshold signal after a fixed delay or after the identification of the peak at the external electrodes, switches on current source for planar electrode. As the circuitry for the planar electrode is floating, opto-couplers are used. A current source for the planar electrodes is connected through a switching logic to the planar electrodes. Switching logic toggles the electrode from a "source electrode" to a "sink electrode" to avoid the problems related to polarization. By multiplexing the signal, the required planar electrodes are selected. Care is taken that the current source is not saturated when it is not connected to the planar electrodes.

The electrodes are connected to the data-acquisition system by short-lengths of co-axial cable to reduce the effect of extraneous noise and interference. The signal source should be placed as close to the electrodes as possible. The outer sheath of the co-axial cable is coupled to the feedback path of a voltage buffer to provide further noise immunity and the inner core is capacititively coupled to the input of the voltage buffer.

Figure 17:
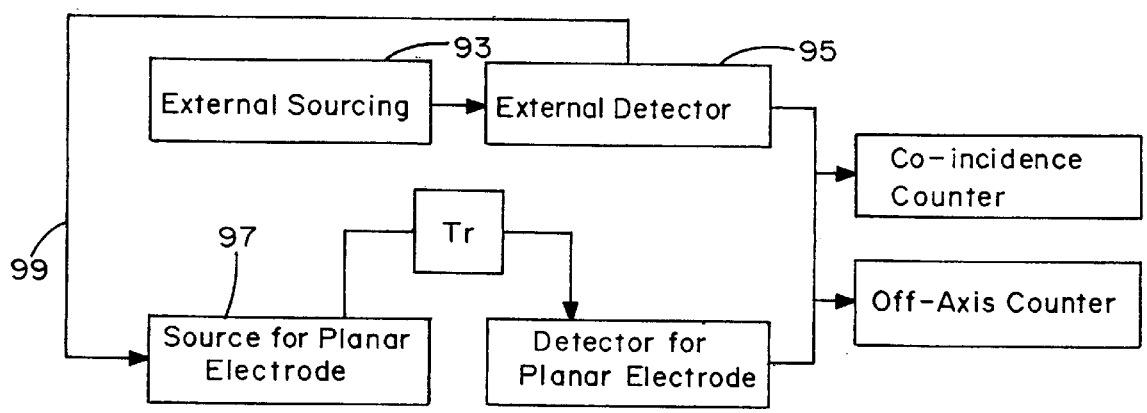
FIG. 17 is a block diagram view showing the relationship between the electrodes, the signal generating circuitry, and the signal analysis circuitry.

FIG. 17 illustrates the block of diagram the circuitry that can be used for avoiding polarization of the planar electrodes and shows an embodiment for measuring co-incidence count and for correcting off-axis error. A constant voltage source or current source 93 is connected to the external electrodes 40, 42. A detector 95 for the external electrodes measures the changes in the electric field in the aperture 62 due to the passage of a particle through the aperture. By comparing the signal on the external electrodes with a voltage just above the noise floor, a threshold pulse is generated. The rising edge of the threshold pulse can be used for activating a current or voltage source 97 for planar electrodes, via path 99. Another arrangement activates the source 97 for the planar electrodes after the measurement of the peak at the external electrodes. The trailing edge of the threshold pulse can be used for switching off the source 97 of planar electrodes or it can be switched off after a fixed delay. By implementing make-before-break switches, switching noise can be reduced. The advantage of this mechanism is that the planar electrodes are active for a short periods of time, typically the transit time through the aperture, which could be as low as few micro-seconds, and therefore do not polarize. Moreover, the planar electrodes can be toggled, e.g., activated with different polarity, each time. This further reduces the probability of electrode polarization.

Indeed, this invention overcomes many drawbacks suffered by the prior art designs. For example, the present invention is not significantly affected by activity that would cause extended sensing zone errors in other designs because the planar electrodes are spaced sufficiently away from the end of the aperture, causing the significant portion of the electric field to be restricted in the aperture itself without spreading outside the aperture. Therefore, the presence of a particle outside the aperture has no significant influence on the measurement. As shown in the FIG. 9, the substrate 66 restricts the electric field to a narrow volume within the aperture. It is desirable to have the diameter of the aperture as narrow as possible so that the influence of a single particle can be detected.

The invention allows for the use of a desirable long aperture therewith because the electrodes are disposed inside the aperture walls and are be positioned quite close together. Such was not possible with other prior art apertures having external electrodes, because the longer the aperture was, the wider the pulse produced. So if a long aperture was used to get good flow characteristics, it also broadened the pulse width, thereby decreasing the counting rate attainable. A long aperture is desirable because it smooths out turbulence and other non-linearity affecting the cell movements before readings are taken.

In hitherto known apparatuses for the analysis of blood samples the recirculated erythrocytes generate weak measuring signals which are approximately of the order of magnitude of the signals which normally are produced by the much smaller thrombocytes. With the proposed method and the proposed apparatus the recirculated erythrocytes do not produce any disturbance or interference signals, so that it is thus possible to count and to measure the erythrocytes and thrombocytes in the same sample. Thus the need for lysis of the erythrocytes is eliminated, thereby making the sample preparation quicker, simpler and less expensive.

With the use of multiple planar electrodes, detailed information on the shape of the particles can be obtained. As such there is no restriction on the number of planar electrodes that can be employed for sensing the particle. Thus, arrangements of 2, 3, 4, 6, 8, 12, and 16 electrodes in a single plane is possible and more advantageously with multiple pairs of planar electrodes. Moreover, these configurations can be repeated along the length of the aperture as described further herein. The signal obtained at the measuring electrodes is fed to the image reconstruction system that is used for forming an image of the particle. Accuracy of the system can be enhanced by implementing an adaptive process to produce the best currents to distinguish the unknown conductivity from a homogeneous conductivity. The ease with which electric currents can be switched from electrode to electrode, and the ease with which the voltages can be measured, gives impedance imaging certain advantages and practical attributes. These attributes include: high speed data acquisition, minimal electronics, low cost and portability.

For the given dimensions of the transducer and for a given kind of particle suspended in a fluid, the best currents for establishing the constricted electrical path are calculated. These given values of currents are fed through active electrodes to form a constricted electrical path. The passive electrodes measure the change in current or voltage. These measurements serve as inputs to image reconstruction system or impedance tomography system. Tomography algorithms converge very fast if the initial value can be estimated reasonably accurately. Initial estimates can be obtained from the measurements at the external electrodes. Reasonably fast and good estimates of the particle shape can be obtained this way.

Additionally, some prior designs have assumed a "shape factor" to amiliorate orientation errors and to compensate for their inability to get accurate readings. For instance, if an extremely elongated particle is assigned a shape factor of 1.0, then the spherical particle of the same volume has a shape factor of 1.5. However, merely assuming a shape factor can lead to accuracies that may be significant. Moreover, these inaccuracies may be exaggerated due to the relative deformability of the particles. Thus, the ability of the current invention to obtain readings from plural transverse angles across the flow aperture can help to rectify this problem.

In another embodiment of the invention, the cross-sectional position of the particle in the hole of the transducer is determined. It includes systems for distinguishing between a particle moving in the center of the hole and a particle moving close to the wall of the hole. Process tomography provides real-time cross-sectional images of the distribution of materials in a process. By analyzing two suitably spaced images, it is possible to measure the direction and speed of material movement. It is possible to distinguish between the particles that are traveling in the center and those which are traveling near the walls of the aperture. This knowledge is used to correct the size obtained using the voltages measured at the external electrodes by applying corrections well known in the art.

Figure 16:
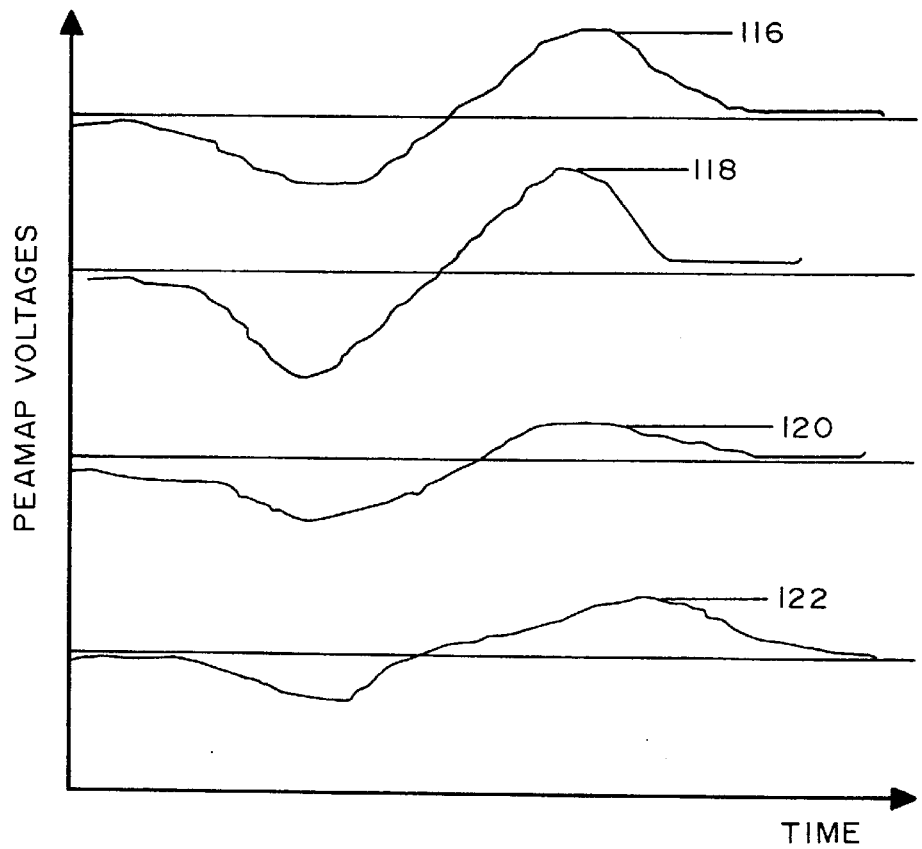
FIG. 16 illustrates the bi-phasic signal expected at the planar electrodes due to the passage of the particle through the aperture when only the external electrodes are active.

Impedance measurement can also be done using all the planar electrodes of one plane in passive mode. When the particle traverses the aperture, it creates a bi-phasic pulse on the passive planar electrodes. When the particle is present inside the aperture the resistance of the zone between the planar electrodes and the external electrode, from which side the particle has entered, is increased. This leads to the change in the voltage of the planar electrodes. The resistance between the planar electrode and the other external electrode increases when the particle crosses the planar electrode. This again alters the voltage on the planar electrodes. FIG. 16 illustrates the bi-phasic signal 116, 118, 120, 122 expected at the planar electrodes due to the passage of the particle through the aperture when only the external electrodes are active. This data is fed into the impedance tomography algorithm to get information on the particle conductivity or particle size or particle shape or particle position or a combination thereof. Obviously an iterative approach to the calculation of these parameters would give the best results. The starting point estimates can be made by using any of the standard techniques well known in the art. The pulse height and the pulse duration are the two important parameters for using fast algorithms. More detailed information can be obtained by applying standard techniques of signal processing like integrating and differentiating the pulse.

The second way to improve the accuracy of the measurement is to examine the shape of the (normally bi-phasic) output signal. A mismatch between the shape and amplitude of the positive and negative phases for each particle passage, or an incorrect time relationship between the two phases indicates a spurious event. This could be a coincidence or a noise spike and is rejected. Finally, for each pulse, the two phases may be averaged, further reducing the noise.

As is appreciated in the art of cytology, any new particle descriptor that can be measured is useful in identifying, analyzing and sorting particles. For example, cells have a membrane of very high resistivity which is in the range of a dielectric. However, the internal portion of the cell is fairly conductive, with different types of particles having varying internal resistivity. Also, it is contemplated that the pathological state of the cell will affect its internal resistivity. Consequently, it is desired to measure this internal resistivity on a cell by cell basis.

The high frequency source, which has a frequency in the radio spectrum or even higher, provides a signal through the orifice simultaneously with the low frequency source,. The two sources produce identifiable signals capable of separate detection when the particle moves through the orifice, one signal being a low frequency (L.F.) signal which is due almost completely to the size of the particles, and the other being a radio frequency (R.F.) signal (being defined as above 1 MHZ) which is due not only to the size, but to the combined effects of size, shape, resistivity and reactance. These output signals are applied by the external electrodes and to a conventional detecting means. The low frequency detector includes a low-pass filter, for preventing the R.F signals from saturating the circuit. If the low frequency is not zero, then demodulating circuitry is included. The R.F. detector includes amplitude modulation detection means for demodulating the R.F. signal.

Multiple planar electrodes can be employed for making measurements at multiple frequencies. Because of the planar structure of the planar electrodes, the inter-electrode capacitance and stray capacitance is significantly lower than that for the planar electrodes. By connecting different frequency sources to different pair of electrodes, interference between the frequency sources can be reduced. Multiple electrodes can also be employed for imaging the permittivity of the particle. Independent information in the impedance data due to the permittivity enhances the instrument's ability to distinguish objects with different interior structure.

With the accurate shape and volume measurements, a precise determination of a particle's resistivity can be extracted from the internal resistance measurement. A precise determination of a particle's resistivity can be extracted from the internal resistance measurements inherent in the R.F. signal. The determination of a particle's resistivity on a particle by particle basis is of great value as a new descriptor for analyzing and identifying biological cells.

In the prior art devices, it was possible to use the R.F. signal to measure the particle's internal resistance, but this measurement has no meaning by itself. This is due to the fact that internal resistance measurement varies not only with the particle's internal resistivity, but also with the size, the shape, and the orientation of the particle. Likewise, in the prior art devices, it was possible to use the first and second impedance signals to measure the particle's opacity, but this measurement varies substantially with the shape, the orientation and the internal resistivity of the particle.

Figure 19:
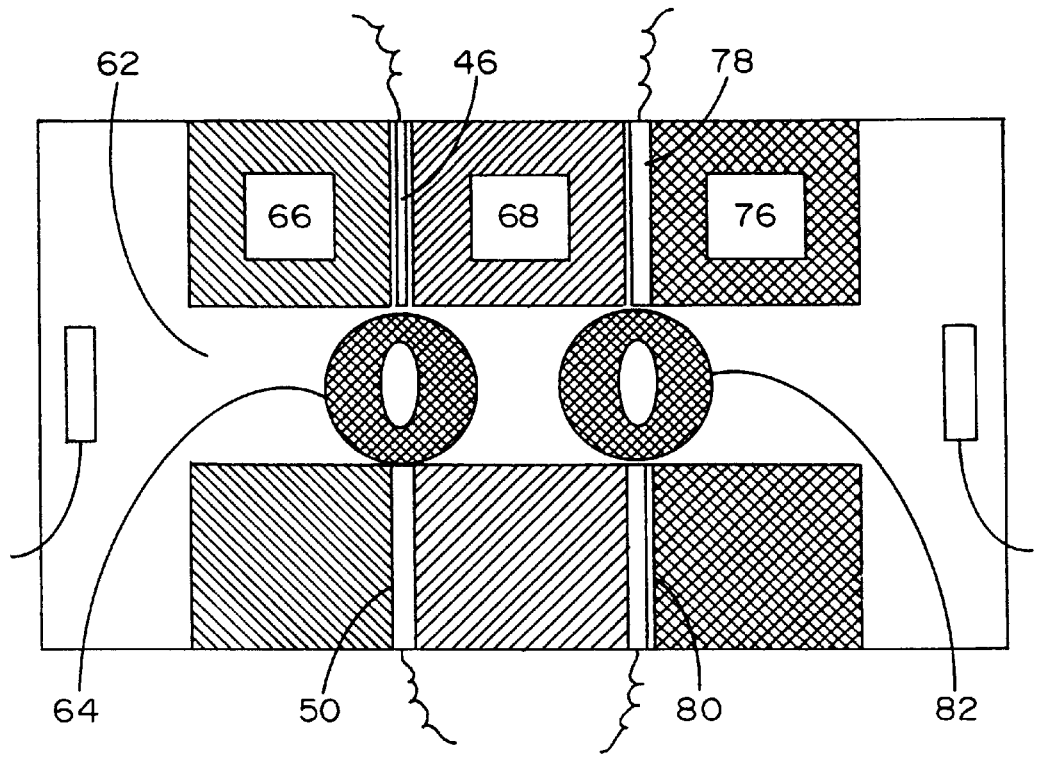
FIG. 19 is a sectional view of an alternative embodiment of the transducer with multiple (two) sets of planar electrodes array along the axis of the aperture.

FIG. 19 is a sectional view of an alternative embodiment of the transducer with multiple sets of planar electrodes arrayed along the axis of the aperture. Multiple electrodes 46, 50 of the first set of planar electrodes create a constricted electrical path 64 and second set of planar electrodes 78, 80 create a downstream second constricted electrical path 82. Depending on the application and method of production the substrates 66, 68, 76 could be same or different. By keeping a sufficient distance, usually equal to few times the aperture diameter between the two sets of planar electrodes, the two constricted electrical paths can be electrically independent of each other. This establishes two constricted electrical paths in succession. Signals obtained from each constricted electrical paths are correlated to improve the signal to noise ratio of the transducer. Signals obtained from the planar electrode arrays are correlated with signals from the external electrodes to further improve the signal to noise ratio.

In another embodiment of the invention, the velocity of the particle while moving in the hole of the transducer is determined. The signal analysis circuitry includes system for calculating the velocity of the particle. Signal correlation circuitry measures the exact time the particle has taken in moving from one constricted electrical path to the second constricted electrical path. Accurate measurement of the velocity of the particle is made possible because of multiple constricted electrical paths. For example, let T be the time required to travel from upstream constricted electrical path to the downstream constricted electrical path. This time can be measured much more accurately as explained below.

The time delay of the fluid is obtained by multiplying the output of downstream constricted electrical path by a time-delayed version of the output of upstream constricted electrical path. The time-delay is adjustable. The product of the two signals is then integrated over a period of time to give the mean value that is called the cross-correlation function. When delta T and the adjustable time delay are unequal, the mean value of the product is small. Only when the fluid time delay and the cross-correlation time delay are equal does the mean value of the product of the signals reach the maximum value. The time delay of the maximum value of the cross correlation function uniquely defines the transit time of particle between the two constricted electrical paths. Dividing the distance between the two constricted electrical paths by the transit time as obtained above, gives the value of the velocity of the particle.

Figure 20:
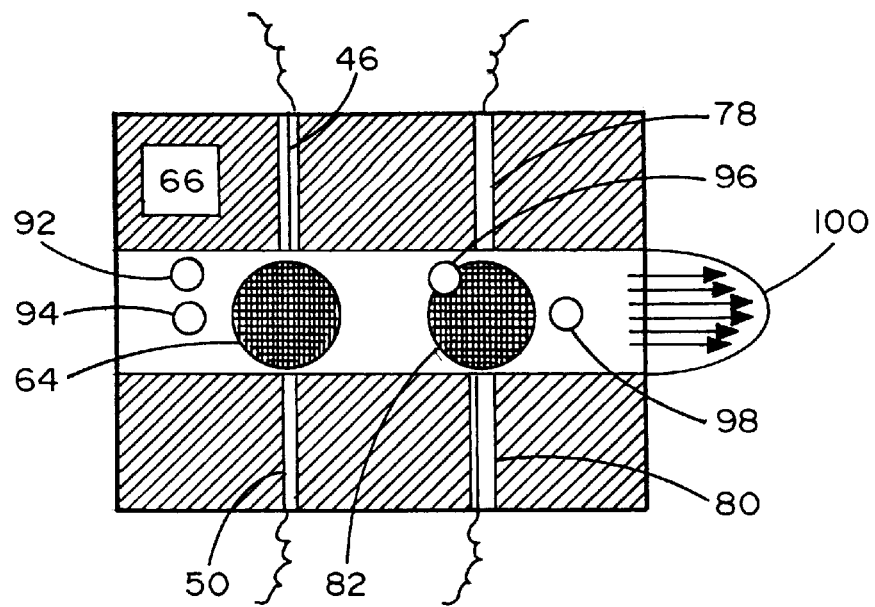
FIG. 20 is a sectional view of the transducer showing two particles entering the aperture simultaneously and being separated in space as they emerge at the end of the aperture because of radial velocity components.

FIG. 20 is a sectional view of the transducer showing two particles 92, 94 entering the aperture simultaneously and being separated in space as they emerge at the end of the aperture because of a radial components of velocity. This embodiment of the invention is used for reducing the coincidence error. This is made possible by comparing the signals obtained from multiple constricted electrical paths. Let two particles 92 and 94, enter the constricted electrical path 64 simultaneously. Let particle 92 be away from the axis and particle 94 be close to the axis. Laminar fluid flow through a circular tube normally follows a radially varying velocity profile (parabolic in the fully-developed channel-flow and flattened, but still reduced at the edges due to growing boundary layers, in a short entrance region) velocity profile 100, wherein the fluid in the center moves faster than the fluid in the periphery. Because of this, particles 92 and 94, which entered the aperture together, are separated in space by the time they reach the second constricted electrical path 82 and have been illustrated as 96 and 98. The simultaneous presence of both the particles in the constricted electrical path of electrode 46 and 50, results in the signal that is due to the combined effect of both the particles. Particle 94 enters the second constricted electrical path 82 after T1, followed by particle 94 after T2 that causes a separate voltage peak. For an abnormally large peak, the signal from the two constricted electrical paths would be analyzed to ascertain if it had arisen because of multiple particles in a constricted electrical path.

Figure 21:
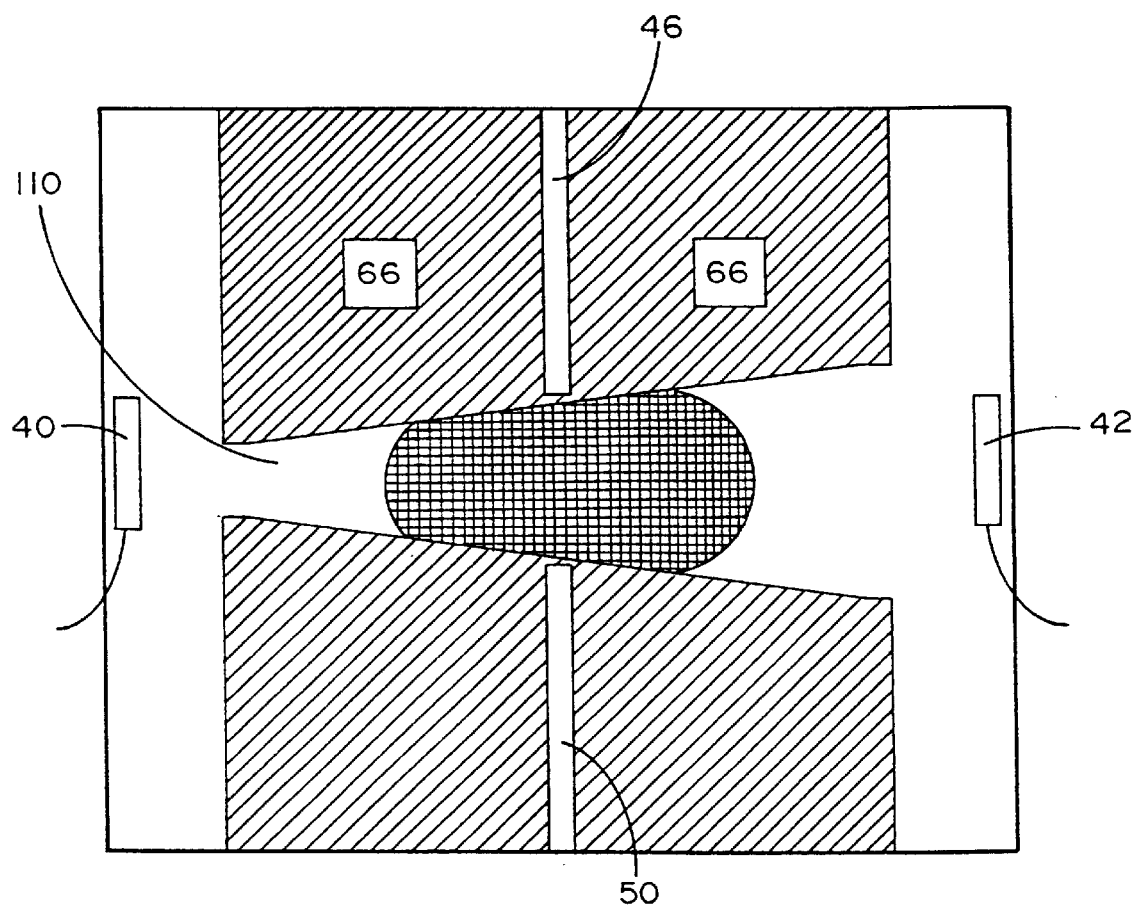
FIG. 21 is a sectional view of an alternative embodiment of the transducer with a tapered aperture.
Figure 22:
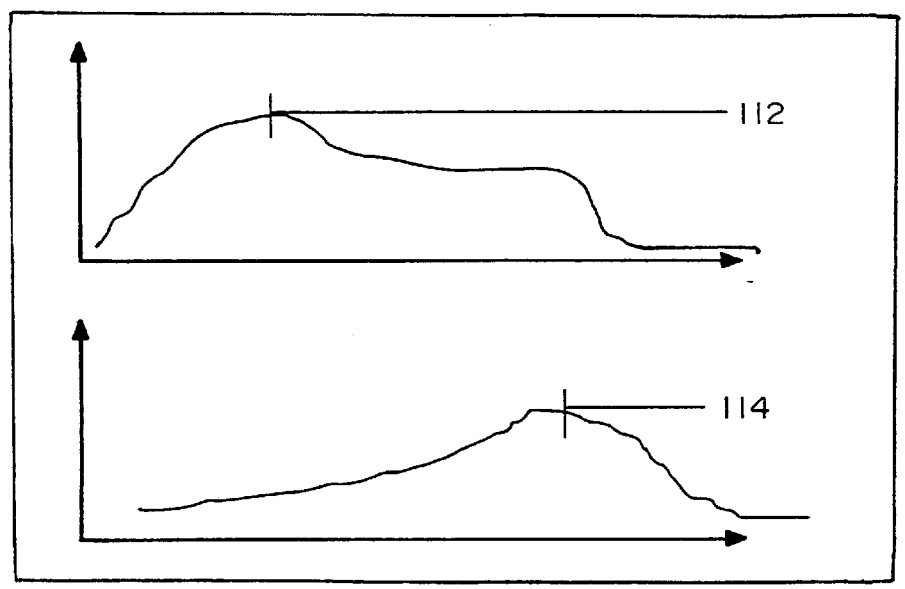
FIG. 22 illustrates the signal expected at external and planar electrodes of the tapered aperture.

FIG. 21 is a sectional view of an alternative embodiment of the transducer with a tapered aperture. FIG. 22 illustrates the signal expected at external and planar electrodes of the tapered aperture. The advantage of the tapered aperture 110 is that the peak 112 of the signal across the external electrodes becomes more pronounced and easier to identify. Planar electrodes 46 and 50 establish another constricted electrical path 64. Peak measured across the planar electrodes occurs exactly when the particle traverses the plane of the planar electrodes. The timing of the peak at the external electrodes and at the planar electrodes is independent of the particle size. FIG. 17 illustrates the block diagram of the circuitry for utilizing the above information to estimate the axial off set of the particle. For example, the peak of the external electrodes may start a counter and the peak of the planar electrodes could stop the counter. This may give an exact measurement of the time taken to travel from the point of minimum aperture diameter to the plane of the planar electrodes. Corrections can be provided for the non-linear movement of the particles and the effect of the fluid drag. This gives an accurate estimate of the velocity of the particle. Velocity of the particle can be utilized to deduce the off-axis position of the particle. Peak value obtained on the external electrodes can be corrected once the exact radical position of the particle is determined.

The above objective of determining the exact time at which the particle traverses a given plane can be achieved by determining the point at which the voltage on the passive planar electrodes crosses the zero line. As illustrated earlier the passive electrodes register a bi-phasic pulse. Instead of using a tapered aperture, the above objective can be achieved by having two sets of planar electrodes at two planes along the axis of the aperture. In an alternative arrangement, a ring electrode may be used to replace a set of planar electrodes in a plane.

Figure 23:
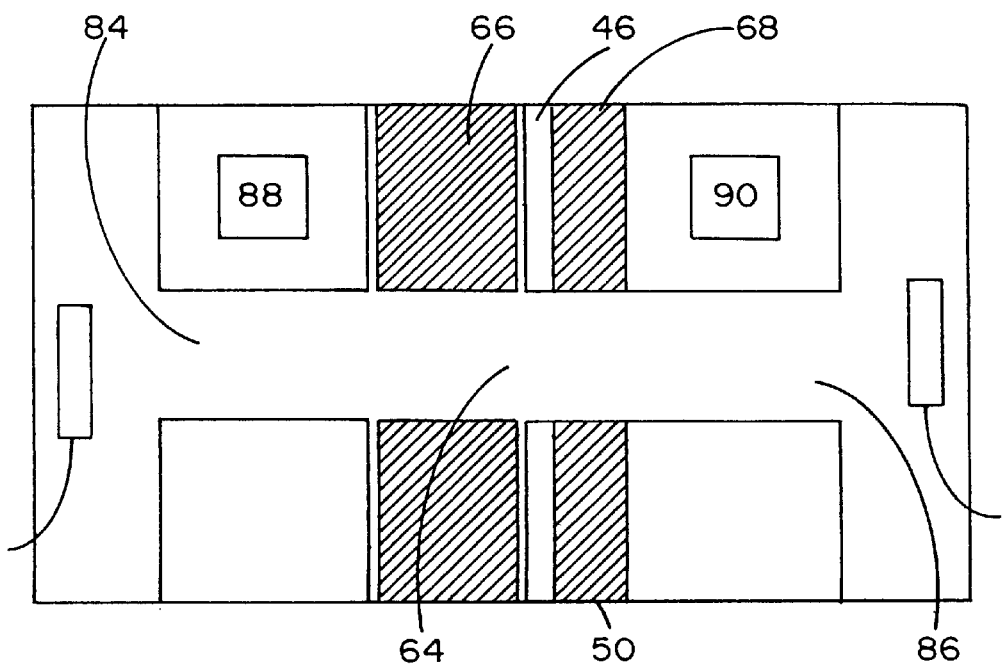
FIG. 23 is a sectional view of an alternative embodiment of the transducer with electrodes for focusing the field of the planar electrode array.

FIG. 23 is a sectional view of an alternative embodiment of the transducer with electrodes for focusing the field of the planar electrode array. Planar electrodes 46, 50 are sandwiched between insulating materials 66, 68. Metal electrodes 88, 89, 90, 91 with a shape identical to the planar electrodes 46, 50 are embedded in the insulating layer close to the plane of the planar electrodes. The thickness of the electrodes is kept sufficiently large and their function is to focus the field of the planar electrodes 46, 50 in the plane of the planar electrodes. Field lines 84 due to focussing electrodes 88, 89 and field lines 86 due to focussing electrodes prevent the field of the planar electrodes from spreading along the axis. Field focussing of the type mentioned above is fairly well known in the art and has significant benefits. By using field focussing the field is restricted to a narrow region thereby intrinsically reducing the probability of co-incidence error. Hence much faster flow can be accepted.

In another embodiment of the invention, the movement of the particle within the transducer is controlled. This can be achieved by controlling the electric field within the transducer and by controlling the pressure differential across the transducer in a desired way. As mentioned earlier, the pressure differential across the transducer can be reversed to change the direction of the particle and to restrict the movement within the transducer.

The apparatus can be used to study time-dependent processes like bacterial and crystal growth by measuring the time evolution of the particle distribution. Pressure reversal techniques coupled with electrical sensing zone method make it possible to study the dynamics of single particle. Because of the presence of two constricted electrical path this transducer would be much more sensitive to the particle movement in the aperture and the particle can be monitored much more accurately. Particularly in the case of charged particles it would be very easy to control the orientation of the particles present in the transducer by controlling the electric field within the transducer.

In another embodiment of the invention, the apparatus further comprises a system for controlling the magnetic field in the transducer to control the movement of the particle, which is magnetically susceptible. Magnetic forces are used for enhancing the efficiency of chemical and bio-chemical separation processes. The imposition of an external and controllable magnetic field is used to influence the motion of magnetically susceptible species. The species of interest are rarely naturally magnetic. Therefore it is necessary to impart appropriate properties to the desired species. Magnetic Carrier Technology involves the labeling of a macromolecule with a magnetic tag, or attachment of the species itself to a larger magnetic carrier.

Many of the enzymes can be immobilized over magnetic fluidized beds. Traditionally, large scale industrial biochemical processes use either soluble enzymes or finely divided mono-cultures of cells to convert a substrate into product. The small size of the biocatalyst presents a major disadvantage in that it is almost impossible to operate such systems continuously. Any throughput of the substrate solution inevitably results in an outflow of the active biocatalyst, resulting in losses. In the case of a homogeneous, soluble enzyme, this loss of bio-catalyst also results in the contamination of the product liquor with active proteins that often requires removal or deactivation. Thus the use of free enzymes and cells is, currently, almost exclusively limited to batch operations. In this embodiment of the invention, the bio-catalyst is tagged on to a magnetic carrier that can be easily trapped in the transducer. This can be done by either controlling the electromagnetic field in the transducer or by controlling the pressure differential across the transducer. The particles carrying the bio-catalyst are moved into the reaction zone and can be called back into the transducer by reversing the pressure differential.

Figure 24:
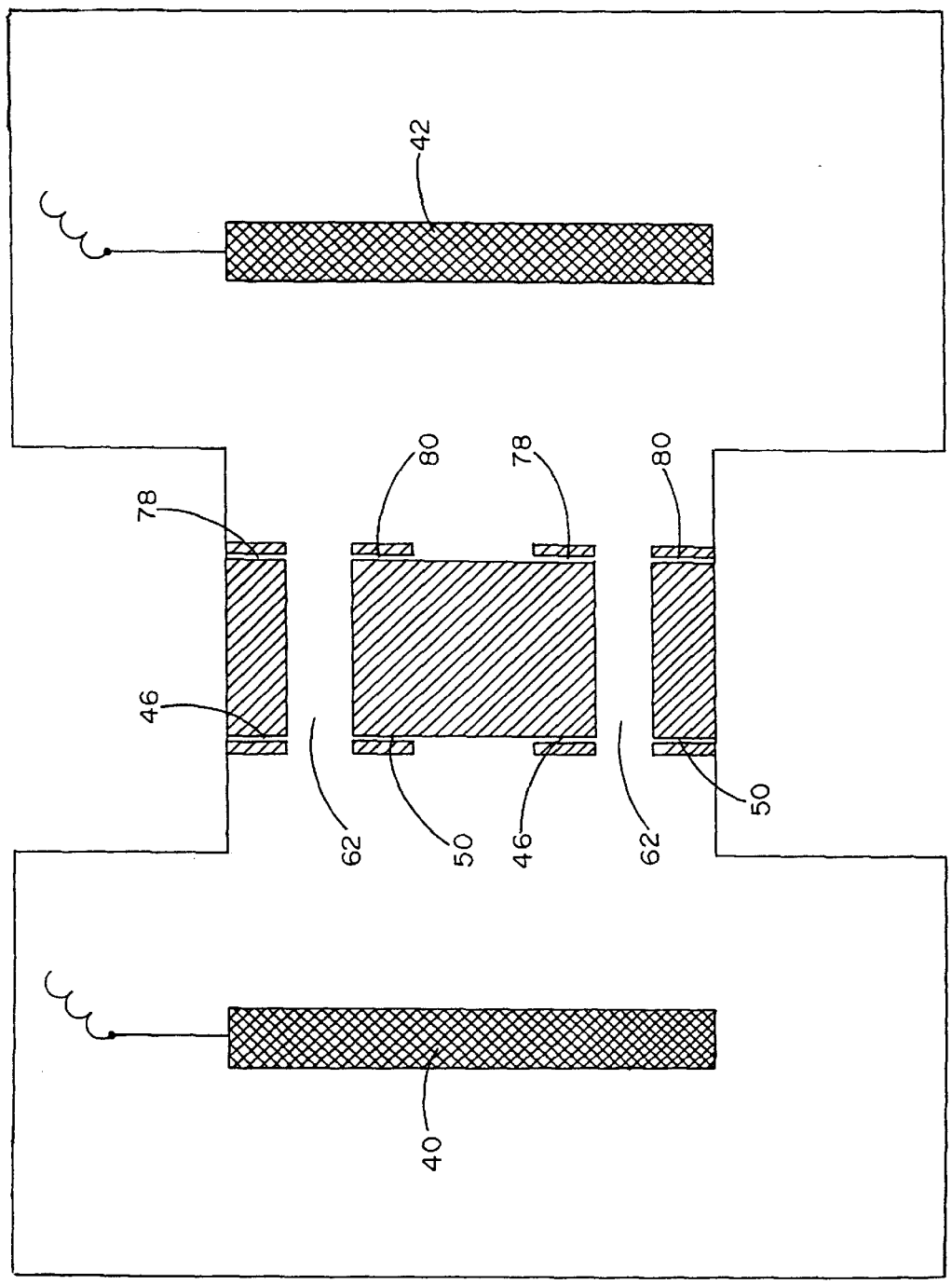
FIG. 24 illustrates a sectional view of a multi-aperture transducer.

In another embodiment of the invention, as shown in FIG. 24, the apparatus comprises multiple holes 250 on the transducer, wherein each constricted electrical path provided thereby includes corresponding elements and behaves like the apertures shown in any of the previous figures. Moreover, each includes an electrical path connected to individual or common signal generating and signal analysis circuitry.

Electroporation can be used for a variety of purposes. For example, it can be used to determine the characteristics of the particles or their membranes or cells so as to detect the influence of foreign agents thereon or of the cells upon other biological systems. For example, the effect of pharmaceutical agents or poisons or other materials on the cells of living organisms, in any concentration, can be evaluated by this system. In addition, the system can be used for investigations into the effect of diseases and biological conditions upon the cells. The system provides information as to the condition and structure of the membranes or the sizes of the particles, the information being useful clinically to detect pathological cells or cell changes which manifest pathological conditions. The technique has also been found useful in determining the effect of chemotherapy or pharmaceutical therapy upon erythrocytes and tissue cells. In the prior art, the particles, usually biological cells, were suspended in a physiological liquid which served as an electrolyte solution which traversed a sensing zone. As the particle traverses the sensing zone the electrodes are energized by a voltage which is increased until dielectric breakdown occurs and the change in the current passing between these electrodes is measured. One of the main limitations of this technique is the lack of control on the orientation of the electric field.

In another embodiment of the invention, the apparatus to address this problem further comprises means for generating a constricted electrical path with a very strong electrical field gradient. In one of the embodiments, the electric field is established by planar electrodes in the downstream. The electric field establishes the critical trans-membrane potential and causes partial and temporary breakdown of cell-membrane. The electric field can be easily controlled so that only a little area of the membrane is broken. When the particle passes through the upstream constricted path, it is identified and the electric field may be established selectively for a certain kind of particles. The electric field may be either a high frequency signal or a high voltage spike. The advantage of using planar electrodes is that not only can the field intensity be controlled but also the direction of the electric field. Thus the shape of the particle and its orientation can be established using the sizing algorithm and, depending on these values, the particle can be subjected to a controlled field for a controlled duration. The above embodiment can be used for determining the dielectric breakdown characteristics of electrolyte-suspended particles having membranes, especially organic cells derived from living organisms, especially liposomes, protoplasts, chloroplasts, vacuole cells or the like and for determining the size of the particles and other characteristics thereof subsequent to dielectric breakdown. Further, electroporation may be accomplished by passing the particles continuously through a measuring opening and each time, while they traverse the opening and are in movement therethrough, subjecting the particles to a linearly increasing electric field (rising, say, to 100 volts) and, from the speed of the particles with respect to the length of the measuring opening or orifice, the electric field and the change in the current through the orifice, determining the dielectric breakdown of the particles, the field strength being sufficient to effect such breakdown. The increase in the current traversing the measuring opening, while a particle is passing therethrough, deviates from linearity and the resulting change in current, by comparison with the linear increase in current through a reference passage not traversed by the particles is an indication of the size of the particle prior to dielectric breakdown and the apparent size of the particle subsequent to dielectric breakdown.

In another embodiment of the invention, a part of the signal generating and signal analysis circuitry is made on the transducer itself. On-chip signal generating and signal analysis circuitry include input pre-amplifiers, a multiplexers, shift registers, test-wave generator and the like. These components are fabricated on the semi-conducting substrate through which the thin hole of the transducer has been drilled, to eliminate the cross talk and stray noise pick-ups. On-chip self test circuitry for testing electrode impedance level can also be provided. On-chip circuitry reduces the number of output leads, thus reducing chip size and the tethering effect of these leads on the probe structure. Secondly, the signal amplification and multiplexing boost the signal levels. This makes the overall system less prone to noise. Additionally, signal buffering reduces the output lead impedance, reducing encapsulation problems. For example, the on-chip signal generating and signal analysis circuitry comprises input pre-amplifiers, analog switches, shift registers, two-phase clock, high speed output buffer, power-on reset, test enable latch, test waveform generator, which has a voltage divider and a 4-stage counter. The power supply for the circuitry is designed to have a fast turn-on time (i.e., 0 to 5 V in 200 ns) so that on-chip electronics can be used to reset the shift register. High input impedance amplifiers placed in close proximity to the planar electrodes would minimize the current drawn from these electrodes and consequently reduce the risk of polarization. Because of the possibility of on-chip circuit analysis, the particles can be identified much more accurately and large number of particles can be separated. However, it should be noted that this system can be used with any known system for separating particles.

In another embodiment of the invention, the apparatus is used for separating different particles. The aperture is connected to a droplet emitting nozzle that has a conducting fluid (sheath) flowing into it through a narrow tube under high pressure. The nozzle is designed to establish laminar flow conditions which provide for more predictable and stable particle trajectories through the channel and also increase the likelihood the sample will be centered in the stream. The fluid carrying the particle along with the sheath is ejected as a minute droplet. The droplets are charged and fall under gravitational force. Along the path of the droplets a controllable electric field is established by the two metal plates connected to signal generating and signal analysis circuitry through connecting wires. After passing through the electric field, the droplets break-up into separate streams and are finally collected in appropriate containers. Because of the possibility of on-chip circuit analysis, the particles can be identified much more speedily and accurately and as a result large number of particles can be separated.

In another embodiment of the invention, the apparatus distinguishes between signals arising due to the passage of different kinds of particles through the transducer. Circuitry for distinguishing particles takes input from measuring electrodes, a system for signal correlation, a system for impedance computer tomography, a system for shape analysis, a system for velocity measurement, a system for identifying off-axis particles and a system for eliminating co-incidence error. The exact nature of combining these systems would depend on the particles to be distinguished, the nature of the fluid and the size of constricted electrical path. Clearly, signal generator and signal analysis circuitry for the several kinds of transducers mentioned above would clearly depend on the specific use of the apparatus and the level of accuracy desired.

In one embodiment of the invention, the signal at the external electrode is sampled after a fixed delay after the particle has traversed the plane of the planar electrodes. If all the planar electrodes are in the passive a mode the point of crossing of the plane of the planar electrodes is the point at which the bi-phasic signal crosses the zero line. If the planar electrodes establish a constricted electrical path, the point of crossing of the plane of the planar electrodes is the point at which the peak occurs at the planar electrodes. It should be apparent that the signal on the external electrodes would be sampled only if the planar electrodes register a particle, and not then when the particle is recirculated due to turbulence. Additionally, there are locations of the channel where the boundary or fringe effect of the measuring field is not effective, i.e., when the particle is momentarily disposed at such a location that the instantaneous or momentary measuring value is practically dependent only upon the particle size and not upon the path of travel of the particle. The sampling operation can be triggered at that point in time when the particle is disposed at such an advantageous location so that the sampling value also is not disturbed by the boundary effects of the measuring field.

While particular embodiments of the invention have been shown and described, it is recognized that various modification will occur to those skilled in the art. For example, the number and locations of planar electrodes may be varied as desired. Accordingly, the scope of the herein described invention shall be limited solely by the claims.

What is claimed is:

1. An apparatus for analyzing particles suspended in a fluid having electrical properties different from that of the particles, as the fluid and articles move from a first fluid containing portion to a second fluid containing portion, the apparatus comprising:

a conduit creating a path permitting fluid communication between the first and second containing portions, said path having a longitudinal axis and said conduit defining a fluid constraining path in a direction along said longitudinal axis;

a first pair of electrodes, said first pair of electrodes including a first electrode located in the first fluid containing portion and a second electrode located in the second fluid containing portion;

a first constricted electrical path between the first and second electrodes, said first constricted electrical path extending along said fluid constraining path; and a second pair of electrodes, said second pair of electrodes including a third electrode and a fourth electrode, said third and fourth electrodes being positioned in a non-encircling arrangement and defining a unique line therebetween extending in a direction transverse to said longitudinal axis, wherein said line between said third and fourth electrodes extends in a direction substantially perpendicular to said longitudinal axis.

2. An apparatus for analyzing particles suspended in a fluid having electrical properties different from that of the particles, as the fluid and particles move from a first fluid containing portion of a second fluid containing portion, the apparatus comprising:

a conduit creating a path permitting fluid communication between the first and second containing portions, said path having a longitudinal axis and said conduit defining a fluid constraining path in a direction along said longitudinal axis;

a first pair of electrodes, said first pair of electrodes including a first electrode located in the first fluid containing portion and a second electrode located in the second fluid containing portion;

a first constricted electrical path between the first and second electrodes, said first constricted electrical path extending along said fluid constraining path;

a second pair of electrodes, said second pair of electrodes including a third electrode and a fourth electrode, said third and fourth electrodes being positioned in a non-encircling arrangement and defining a unique line therebetween extending in a direction transverse to said longitudinal axis; and a third pair of electrodes, said third pair of electrodes including a fifth electrode and sixth electrode and defining a unique line therebetween, said line between the fifth and sixth electrodes extending in a direction transverse to the longitudinal axis and transverse to the line between the third and fourth electrodes.

3. The apparatus of claim 2, wherein said line between said third and fourth electrodes extends substantially in a direction perpendicular to said longitudinal axis wherein said line between said fifth and sixth electrodes extends in a direction substantially perpendicular to said longitudinal axis and substantially perpendicular to said line between the third and fourth electrodes.

4. The apparatus of claim 2, wherein the second and third pair of electrodes lie in substantially the same plane.

5. An apparatus for analyzing particles suspended in a fluid having electrical properties different from that of the particles, as the fluid and particles move from a first fluid containing portion to a second fluid containing portion, the apparatus comprising:

a first pair of electrodes, said first pair of electrodes including a first electrode located in the first fluid containing portion and a second electrode located in the second fluid containing portion;

a first constricted electrical path between the first and second electrodes, said first constricted electrical path extending along said fluid constraining path;

a plurality of conduits each creating a corresponding distinct path for permitting fluid communication between the first and second fluid containing portions, each said path having a respective longitudinal axis and a second pair of electrodes respectively associated with each conduit and defining a respective line between each said second pair of electrodes, wherein each respective line extends in a direction transverse to its said respective longitudinal axis.

6. An apparatus for analyzing particles suspended in a fluid having electrical properties different from that of the particles, as the fluid and particles move from a first fluid containing portion to a second fluid containing portion, the apparatus comprising:

a conduit creating a pat permitting fluid communication between the first and second containing portions, said path having a longitudinal axis and said conduit defining a fluid constraining path in a direction along said longitudinal axis;

a first pair of electrodes, said first pair of electrodes including a first electrode located in the first fluid containing portion and a second electrode located in the second fluid containing portion;

a first constricted electrical path between the first and second electrodes, said first constricted electrical path extending along said fluid constraining path; and a second pair of electrodes, said second pair of electrodes including a third electrode and a fourth electrode, said third and fourth electrodes being positioned in a non-encircling arrangement and defining a unique line therebetween extending in a direction transverse to said longitudinal axis, wherein said conduit includes an interior wall, said third and fourth electrodes having a sensor portion located substantially at the conduit interior wall.

7. An apparatus for analyzing particles suspended in a fluid having electrical properties different from that of the particles, as the fluid and particles move from a first fluid containing portion to a second fluid containing portion, the apparatus comprising:

a conduit creating a path permitting fluid communication between the first and second containing portions, said path having a longitudinal axis and said conduit defining a fluid constraining path in a direction along said longitudinal axis;

a first pair of electrodes, said first pair of electrodes including a first electrode located in the first fluid containing portion and a second electrode located in the second fluid containing portion;

a first constricted electrical path between the first and second electrodes, said first constricted electrical path extending along said fluid constraining path; and a second pair of electrodes, said second pair of electrodes including a third electrode and a fourth electrode, said third and fourth electrodes being positioned in a non-encircling arrangement and defining a unique line therebetween extending in a direction transverse to said longitudinal axis, wherein said conduit includes an internal wall surface, and said apparatus further includes a first aperture and a second aperture in said conduit internal wall surface, said first and second apertures being substantially aligned and located on opposite sides of the conduit, wherein said third electrode is positioned in said first aperture and said fourth electrode is positioned in said second aperture.

8. An apparatus for analyzing particles suspended in a fluid having electrical properties different from that of the particles, as the fluid and particles move from a first fluid containing portion to a second fluid containing portion, the apparatus comprising:

a conduit creating a path permitting fluid communication between the first and second containing portions, said path having a longitudinal axis and said conduit defining a fluid constraining path in a direction along said longitudinal axis;

a first pair of electrodes, said first pair of electrodes including a first electrode located in the first fluid containing portion and a second electrode located in the second fluid containing portion;

a first constricted electrical path between the first and second electrodes, said first constricted electrical path extending along said fluid constraining path; and a second pair of electrodes, said second pair of electrodes including a third electrode and a fourth electrode, said third and fourth electrodes being positioned in a non-encircling arrangement and defining a unique line therebetween extending in a direction transverse to said longitudinal axis, wherein said conduit includes an internal cross-sectional area defined in a direction perpendicular to said longitudinal axis, said cross-section area remaining substantially constant between the first and second fluid containing portions.

9. An apparatus for analyzing particles suspended in a fluid having electrical properties different from that of the particles, as the fluid and particles move from a first fluid containing portion to a second fluid containing portion, the apparatus comprising:

a conduit creating a path permitting fluid communication between the first and second containing portions, said path having a longitudinal axis and said conduit defining a fluid constraining path in a direction along said longitudinal axis;

a first pair of electrodes, said first pair of electrodes including a first electrode located in the first fluid containing portion and a second electrode located in the second fluid containing portion;

a first constricted electrical path between the first and second electrodes, said first constricted electrical path extending along said fluid constraining path; and a second pair of electrodes, said second pair of electrodes including a third electrode and a fourth electrode, said third and fourth electrodes being positioned in a non-encircling arrangement and defining a unique line therebetween extending in a direction transverse to said longitudinal axis, wherein said conduit includes an internal cross-sectional area defined in a direction perpendicular to said longitudinal axis, said cross-section area increasing between the first and second fluid containing portions a direction of fluid flow through the conduit.

10. An apparatus for analyzing particles suspended in a fluid having electrical properties different from that of the particles, as the fluid and particles move from a first fluid containing portion to a second fluid containing portion, the apparatus comprising:

a conduit creating a path permitting fluid communication between the first and second containing portions, said path having a longitudinal axis and said conduit defining a fluid constraining path in a direction along said longitudinal axis;

a first pair of electrodes, said first pair of electrodes including a first electrode located in the first fluid containing portion and a second electrode located in the second fluid containing portion;

a first constricted electrical path between the first and second electrodes, said first constricted electrical path extending along said fluid constraining path;

a second pair of electrodes, said second pair of electrodes including a third electrode and a fourth electrode, said third and fourth electrodes being positioned in a non-encircling arrangement and defining a unique line therebetween extending in a direction transverse to said longitudinal axis;

a controller, said controller being electrically coupled to all of said electrodes and having signal analysis circuitry for determining characteristics of the particles; and an electroporation device, said electroporation device being electrically coupled to the controller to enable the electroporation device to electroporate a particle based on characteristics of the particle.

11. An apparatus for analyzing particles suspended in a fluid having electrical properties different from that of the particles, as the fluid and particles move from a first fluid containing portion to a second fluid containing portion, the apparatus comprising:

a conduit creating a path permitting fluid communication between the first and second containing portions, said path having a longitudinal axis and said conduit defining a fluid constraining path in a direction along said longitudinal axis;

a first pair of electrodes, said first pair of electrodes including a first electrode located in the first fluid containing portion and a second electrode located in the second fluid containing portion;

a first constricted electrical path between the first and second electrodes, said first constricted electrical path extending along said fluid constraining path;

a second pair of electrodes, said second pair of electrodes including a third electrode and a fourth electrode, said third and fourth electrodes being positioned in a non-encircling arrangement and defining a unique line therebetween extending in a direction transverse to said longitudinal axis; and first and second means for focusing an electric field between said second pair of electrodes, said second pair of electrodes being located between said first and second means.

12. An apparatus for analyzing particles suspended in a fluid having electrical properties different from that of the particles, as the fluid and particles move from a first fluid containing portion to a second fluid containing portion, the apparatus comprising:

a conduit creating a pat permitting fluid communication between the first and second containing portions, said path having a longitudinal axis and said conduit defining a fluid constraining path in a direction along said longitudinal axis;

a first pair of electrodes, said first pair of electrodes including a first electrode located in the first fluid containing portion and a second electrode located in the second fluid containing portion;

a first constricted electrical path between the first and second electrodes, said first constricted electrical path extending along said fluid constraining path; and a second pair of electrodes, said second pair of electrodes including a third electrode and a fourth electrode, said third and fourth electrodes being positioned in a non-encircling arrangement and defining a unique line therebetween extending in a direction transverse to said longitudinal axis, wherein said first pair of electrodes are active electrodes and said second pair of electrodes are passive electrodes.

13. An apparatus for analyzing particles suspended in a fluid having electrical properties different from that of the particles, as the fluid and particles move from a first fluid containing portion to a second fluid containing portion, the apparatus comprising:

a conduit creating a pat permitting fluid communication between the first and second containing portions, said path having a longitudinal axis and said conduit defining a fluid constraining path in a direction along said longitudinal axis;

a first pair of electrodes, said first pair of electrodes including a first electrode located in the first fluid containing portion and a second electrode located in the second fluid containing portion;

a first constricted electrical path between the first and second electrodes, said first constricted electrical path extending along said fluid constraining path; and a second pair of electrodes, said second pair of electrodes including a third electrode and a fourth electrode, said third and fourth electrodes being positioned in a non-encircling arrangement and defining a unique line therebetween extending in a direction transverse to said longitudinal axis, wherein said first and second pairs of electrodes are active electrodes.

14. An apparatus for analyzing particles suspended in a fluid having electrical properties different from that of the particles, as the fluid and particles move from a first fluid containing portion to a second fluid containing portion, the apparatus comprising:

a conduit creating a pat permitting fluid communication between the first and second containing portions, said path having a longitudinal axis and said conduit defining a fluid constraining path in a direction along said longitudinal axis;

a first pair of electrodes, said first pair of electrodes including a first electrode located in the first fluid containing portion and a second electrode located in the second fluid containing portion;

a first constricted electrical path between the first and second electrodes, said first constricted electrical path extending along said fluid constraining path; and a second pair of electrodes, said second pair of electrodes including a third electrode and a fourth electrode, said third and fourth electrodes being positioned in a non-encircling arrangement and defining a unique line therebetween extending in a direction transverse to said longitudinal axis, wherein said first and second pairs of electrodes are capable of being active and passive electrodes, said apparatus further comprising a controller capable of switching said first and second set of electrodes between a passive mode and an active mode.

15. An apparatus for analyzing particles suspended in a fluid having electrical properties different from that of the particles, as the fluid and particles move from a first fluid containing portion to a second fluid containing portion, the apparatus comprising:

a conduit creating a path permitting fluid communication between the first and second containing portions, said path having a longitudinal axis and said conduit defining a fluid constraining path in a direction along said longitudinal axis;

a first pair of electrodes, said first pair of electrodes including a first electrode located in the first fluid containing portion and a second electrode located in the second fluid containing portion;

a first constricted electrical path between the first and second electrodes, said first constricted electrical path extending along said fluid constraining path;

a second pair of electrodes, said second pair of electrodes including a third electrode and a fourth electrode, said third and fourth electrodes being positioned in a non-encircling arrangement, and defining a unique line therebetween extending in a direction transverse to said longitudinal axis;

a third pair of electrodes, said third pair of electrodes including a fifth electrode and a sixth electrode and defining a corresponding line therebetween extending in a direction transverse to the longitudinal axis and transverse to said direction of the line between the third and fourth electrodes;

a fourth pair of electrodes located downstream from said second and third pairs of electrodes, said fourth pair of electrodes including a seventh electrode and eighth electrode and defining a corresponding line between said seventh and eighth electrodes extending in a direction transverse to said longitudinal axis; and a fifth pair of electrodes located downstream from said second and third pairs of electrodes, said fifth pair of electrodes including a ninth electrode and a tenth electrode and defining a corresponding line between said ninth and tenth electrodes extending in a direction transverse to the longitudinal axis and transverse to said direction of the line between the seventh and eighth electrodes.

16. An apparatus for analyzing particles suspended in a fluid having electrical properties different from that of the particles, as the fluid and particles move from a first fluid containing portion to a second fluid containing portion, said apparatus comprising:

a conduit creating a path permitting fluid communication between the first and second containing portions, said path having a longitudinal axis, said conduit defining a fluid constraining path in a direction along said longitudinal axis;

a first pair of electrodes, said first pair of electrodes including a first electrode and a second electrode;

a constricted electrical path between said first and second electrodes extending in a first direction transverse to said longitudinal axis;

a second pair of electrodes, said second pair of electrodes including a third electrode and a fourth electrode; and a second constricted electrical path between said third and fourth electrodes extending in a direction transverse to said longitudinal axis.

17. The apparatus of claim 16, wherein said first and second constricted electrical paths are transverse to each other.

18. The apparatus of claim 17, wherein said first and second constricted electrical paths are perpendicular to each other.

19. The apparatus of claim 17, wherein said first and second electrodes are positioned in a non-encircling arrangement, and said third and fourth electrodes are positioned in a non-encircling arrangement.

20. The apparatus of claim 16, further comprising a third pair of electrodes, said third pair of electrodes including a fifth electrode located in the first fluid containing portion and a sixth electrode located in the second fluid containing portion.

21. A method for analyzing the size of individual particles suspended in a fluid having electrical properties different from that of the particles, said method comprising:

providing a first fluid containing portion and a second fluid containing portion, a conduit in a barrier between the fluid containing portions, a first pair of electrodes between the fluid containing portions at a first location, and a second pair of electrodes between the fluid containing portions at second location position downstream from the first location;

determining the maximum velocity of particles traveling through the conduit;

determining the actual velocity of a particle traveling through the conduit between the first and second pair of electrodes;

measuring the electrical impedance of the particle traveling through the conduit; and adjusting the measured impedance of the particle based on a relationship between the determined actual velocity and the determined maximum velocity.

22. The apparatus of claim 1, wherein only respective tips of the third and fourth electrodes are exposed to the fluid.

23. The apparatus of claim 22, wherein said tips are coated with an area-increasing material.

24. The apparatus of claim 23, wherein said area-increasing material comprises platinum black.

25. The apparatus of claim 1, wherein said second pair of electrodes are sized to be disposed within said fluid-constraining path, such that a significant portion of an electric field generated therebetween is restricted to be within the conduit.

26. The apparatus of claim 15, further comprising a pair of insulating layers disposed to sandwich at least said second pair of electrodes therebetween.

27. The apparatus of claim 26, wherein at least one of said third or fourth pair of electrodes is disposed within one of said pair of insulating layers.

28. The apparatus of claim 1, wherein said second pair of electrodes provides an electric field of an intensity sufficient to cause partial and temporary breakdown of a cell-membrane of said particles for enabling determination of a dielectric characteristic of said particles.

29. The apparatus of claim 1, further comprising at least one of signal generating and signal analysis circuits located on an element in which said conduit is located.

30. The apparatus of claim 1, further comprising a droplet emitting nozzle through which a high pressure conducting fluid carrying said particles is flowed laminarly.

31. The apparatus of claim 30, further comprising two metal plates for providing an electric field through which a discharge of said laminar flow is passed.

32. The apparatus of claim 31, wherein said discharge forms small droplets which separate in accordance with the sizes of particles contained within said droplets.

33. The apparatus of claim 32, further comprising containers to collect said separated droplets and said respectively sized particles contained therein.

* * * * *